(12) United States Patent
Geraths et al.

(10) Patent No.: US 11,008,414 B2
(45) Date of Patent: May 18, 2021

(54) POLYMER MATERIALS FOR CONTACT LENS APPLICATIONS

(71) Applicant: CIS Pharma AG, Bubendorf (CH)

(72) Inventors: Christian Geraths, Rheinfelden (DE); Rolf Schäfer, Arisdorf (CH)

(73) Assignee: CIS PHARMA AG, Bubendorf (CH)

( * ) Notice: Subject to any disclaimer, the term of this patent is extended or adjusted under 35 U.S.C. 154(b) by 554 days.

(21) Appl. No.: 15/932,509

(22) PCT Filed: Sep. 30, 2016

(86) PCT No.: PCT/EP2016/073407
§ 371 (c)(1),
(2) Date: Mar. 8, 2018

(87) PCT Pub. No.: WO2017/055536
PCT Pub. Date: Apr. 6, 2017

(65) Prior Publication Data
US 2020/0283560 A1    Sep. 10, 2020

Related U.S. Application Data

(60) Provisional application No. 62/284,527, filed on Oct. 2, 2015.

(51) Int. Cl.
| B29D 11/00 | (2006.01) |
| C07C 231/02 | (2006.01) |
| C07C 319/12 | (2006.01) |
| C07D 207/16 | (2006.01) |
| C08F 220/20 | (2006.01) |
| C08L 83/04 | (2006.01) |
| C08F 293/00 | (2006.01) |
| C08F 222/38 | (2006.01) |
| G02B 1/04 | (2006.01) |
| B29K 105/00 | (2006.01) |

(52) U.S. Cl.
CPC ...... *C08F 293/005* (2013.01); *B29D 11/0025* (2013.01); *C07C 231/02* (2013.01); *C07C 319/12* (2013.01); *C07D 207/16* (2013.01); *C08F 220/20* (2013.01); *C08F 222/38* (2013.01); *C08L 83/04* (2013.01); *G02B 1/043* (2013.01); *B29K 2105/0061* (2013.01); *C08F 2438/03* (2013.01); *C08L 2203/02* (2013.01)

(58) Field of Classification Search
None
See application file for complete search history.

(56) References Cited

U.S. PATENT DOCUMENTS

| 2009/0103045 A1 | 4/2009 | Lai et al. |
| 2009/0232871 A1* | 9/2009 | Hitz ............... A61L 15/24 424/429 |
| 2012/0231072 A1 | 9/2012 | Kang-Mieler et al. |

* cited by examiner

Primary Examiner — Jeffrey D Washville
(74) Attorney, Agent, or Firm — Richard Voellmy

(57) ABSTRACT

The present invention relates to copolymers made from a polymerization mixture comprising (a) one or more polymerizable monomers, which monomers are characterized as having at least one vinylic group and not containing an amino acid residue, (b) one or more not-functionalized side chain-linked amino acids, (c) one or more functionalized side chain-linked amino acids, (d) a free radical initiator and, optionally, (e) a chain-transfer-agent. It also relates to block copolymers comprising the same monomers. The invention also encompasses silicone hydrogel contact lenses coated with or comprising the latter copolymers and block copolymers as well methods for introducing the copolymers and block copolymers into silicone hydrogel contact lenses.

18 Claims, 7 Drawing Sheets 1  2  3  4

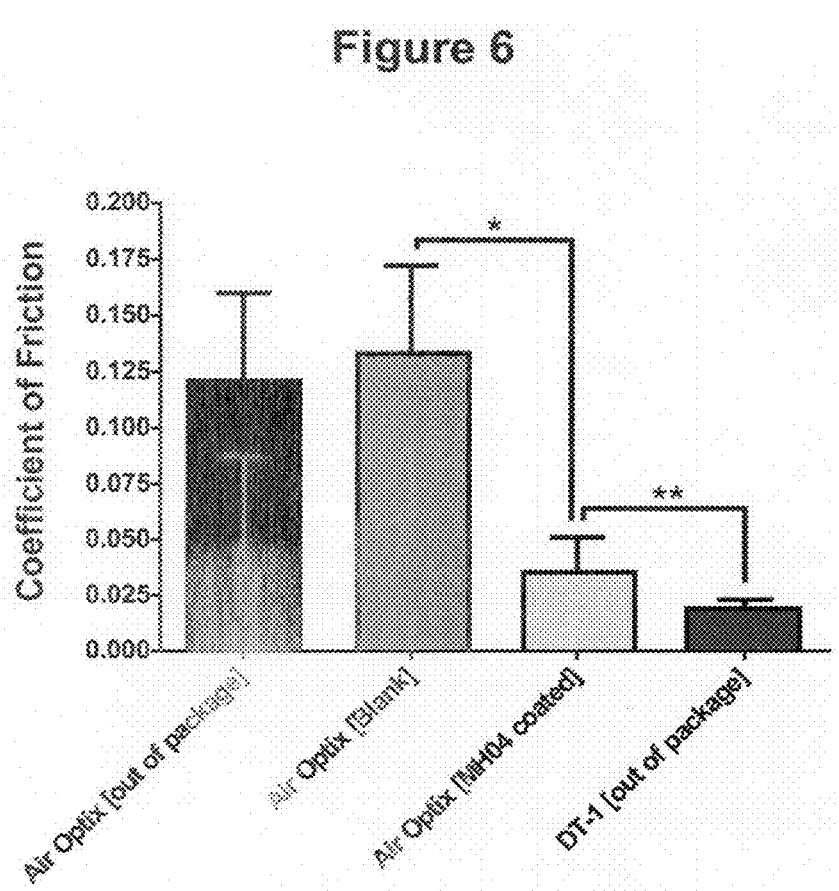

POLYMER MATERIALS FOR CONTACT LENS APPLICATIONS

FIELD OF THE INVENTION

The invention relates to silicone hydrogel contact lenses comprising leachable polymers or copolymers serving as wetting and lubricating agents. The polymers or copolymers comprise monomers with side chain-linked amino acids having free alpha-amino and alpha-carboxyl groups. Further, the invention relates to copolymers, preferably block copolymers, containing hydrophilic monomers that are not-functionalized side chain-linked amino acids as well as hydrophobic monomers that are functionalized side chain-linked amino acids. In the latter monomers alpha-amino and/or alpha-carboxyl groups of amino acids are functionalized with alkyl or cholesten residues to mimic lipid structures. The latter block copolymers should improve the wettability and lubricity of the surfaces of the silicone hydrogel contact lenses as well as effectively shield them against harmful lipid deposits from the tear fluid.

BACKGROUND OF THE INVENTION

A stable uniform tear film over the surface of a contact lens is a key element for good vision. Contact lenses which do not have good wetting characteristics cause rapid breakup of the lens tear film and a consequent reduction in vision. A stable lens tear film also provides a lubricating effect resulting in comfortable lid movement over the surface of the lens. A wettable contact lens also stabilizes a continuous tear film between the surface of the lens and the cornea. Contact lens surface characteristics influence biocompatibility. A poorly wettable or poorly lubricious contact lens causes acceleration of tear film deposits especially when portions of the lens surface dry out [1, 2]. These deposits are composed of proteins and lipids present in the tear film which proteins and lipids tend to bind especially strongly to silicone and silicone-hydrogel lens materials, leading to a reduction of wear comfort and vision [3] [and reference therein].

Friction is the resistance developed between contacting surfaces when one of the bodies moves over the other. The friction coefficient is the ratio of the friction between two surfaces and the force pushing them together. Lubricity is the reciprocal of friction.

Lenses with high friction coefficients cause autoimmune reactions, mechanical irritation of the tarsal conjunctiva and other ocular tissue and in some cases considerable discomfort. A severe consequence has been the development of contact lens papillary conjunctivitis (CLPC) [4, 5]. The development of disposable lenses substantially reduced these problems.

Occurrence of CLPC was observed with the first generation of silicone hydrogel contact lenses. Silicone hydrogel lenses rely on silicon, rather than water, to transport oxygen through the lens.

Currently, there are two broad material classes that chemists use to provide silicon for silicone hydrogel contact lenses: TRIS [(trimethylsiloxysilyl) propyl vinyl carbamate] and siloxy macromers. Three generations of silicon hydrogel lenses were developed in the past using chemistry.

First generation silicone hydrogel lenses use some form of the TRIS molecule and may include siloxy macromers. The Balafilcon A material has a Dk (oxygen transmissibility, a measure of oxygen permeability) of 99 barriers and makes use of a TRIS-based approach to provide the silicon moiety. Bausch & Lomb may have taken advantage of the TRIS molecule during plasma oxidation of the lens surface because oxidation of TRIS produces hydrophilic, glassy silicate islands. Lotrafilcon A employs siloxy macromers in addition to a TRIS-based backbone. It has the highest Dk (140 barriers) of any silicone hydrogel material and also has the highest modulus. Lotrafilcon A took advantage of TRIS and other hydrophilic monomers to phase independently, producing a material that has two distinct phases, a water and a gel phase, which the manufacturer calls co-continuous phases. This allows for high oxygen permeability as well as high water and sodium permeability.

Second-generation lenses are based on the Tanaka monomer which Vistakon improved after the original patent (U.S. Pat. No. 4,235,985) had expired. Galyfilcon A is a mixture of the Tanaka monomer, a siloxy macromer and hydrophilic monomers, 2-hydroxyethyl methacrylate (HEMA) and N,N-dimethylacrylamide (DMA). The lens has a Dk of 60 barriers, the lowest of all the silicone hydrogel lenses, but it has a very high water content 47% (w). Vistakon uses a similar polymer, Senofilcon A, for its Acuvue Oasys lens.

Comfilcon A (Biofinity, CooperVision) was the first third generation polymer. With no TRIS-based derivatives, all of the silicon added to the material's chemistry is based on siloxy macromers which represents a unique way to combine the lens' silicone and water properties. The material uses two siloxy macromers of different sizes that, when used in combination, produce very high oxygen permeability.

The lens has a Dk of 128. Enfilcon A (Avaira, Cooper-Vision) is another third-generation material that is naturally wettable. The Enfilcon A material has 46% water. The lens has a low modulus of 0.5 MPa and a Dk of 100.

Newer silicone hydrogel lenses have a lower frequency of CLPC which is ascribed to an improved lubricity achieved by increased water content and the introduction of methods to retain surface moisture. Conditions described subsequent to the introduction of silicone hydrogel lenses include lid-wiper epitheliopathy (LWE), affecting a band of tissue of the marginal conjunctiva of the upper eyelid that wipes the ocular surface [6]. Lid-parallel conjunctival folds (LIPCOF) which are sub-clinical folds of the bulbar conjunctiva above and parallel of the lower lid margin is a related condition that also appears to be correlated with suboptimal lubricity of the lens [7].

To achieve increased lubricity, efforts were made to enhance the wettability of lenses and their ability to retain moisture during application. One approach was to include wetting agents such as polyvinyl alcohol, polyvinyl pyrrolidone or hyaluronic acid [8]. Another approach is exemplified by the water-gradient silicone hydrogel lens Delefilcon A [9, 10]. The lens has a water content ranging from 33% at the core to about 80% at the surface. A minimally cross-linked thin hydrophilic gel layer is graded on the surfaces of a silicone hydrogel lens. This results in surfaces with very low friction coefficients [10].

Among marketed contact lenses, the wettability of Lotrafilcon A and B lenses was improved by the formation of a permanent, ultrathin, continuous hydrophilic plasma coating with high refractive index. In Balafilcon A, oxidative plasma treatment created a film of hydrophilic silicates on the lens surfaces. Surface treatment of Asmofilcon A made use of a nanoglass technology. Delefilcon A (e.g., Dailies Total 1®, DT-1®, Alcon) lenses are made from two hydrogel materials, of which one is a silicone hydrogel with relatively low water content but high oxygen transmissibility that is present in the core and the other is a non-silicone-containing hydrogel of very high water content that covers the surfaces of the core material. The latter hydrophilic hydrogel layer drastically improves the wear comfort of these lenses. Comfilcon A and Enfilcon A lenses are made from silicone hydrogels that include hydrophilic monomers that diffuse to the lens surfaces, thereby having a lubricating effect. Long chain, high molecular weight agents based on polyvinyl pyrrolidone serve as internal wetting agents in Galyfilcon A, Senofilcon A and Narafilcon A & B lenses. External wetting agents are introduced by lens care solutions containing surfactants, e.g., OptiFree RepleniSH, BioTrue, RevitaLens, or ClearCare. Wettability could also be improved by the addition of polyethylene glycol, hydroxypropyl methylcellulose, polyvinyl alcohol, or polyvinyl pyrrolidone in the packaging solution [8, 11, 12]. The above-mentioned external wetting agents are lost from the lens surface within a fraction of an hour upon ocular application of the lens.

While, as outlined above, multiple approaches have been disclosed that can increase the lubricity of a silicone hydrogel lens, most of these approaches also encompass undesirable features, such as, for example, a requirement for non-standard lens production in multiple steps, inability to thermally sterilize the lenses, or the introduction of monomers or polymers causing low biocompatibility. This invention describes a class of new leachable polymers and copolymers that improve lens lubricity, biocompatibility, comfort and manufacturing of silicon hydrogel lenses as well as are believed to effectively prevent lipid deposition.

SUMMARY OF THE INVENTION

Functionalized and not-functionalized co-principal monomers of the present disclosure are defined by formula I and formula II,

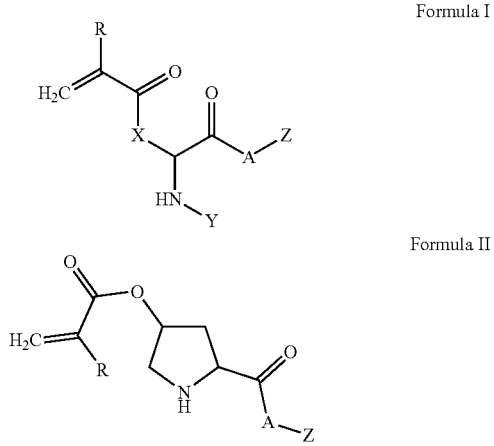

Formula I

Formula II wherein R is —H, —$CH_3$, —$CH_2$—$CH_3$, —$(CH_2)_2$—$CH_3$; X is —$NH(CH_2)_4$—, —$NH(CH_2)_3$—, —O—$C_6H_4$—$CH_2$—, —O—$CH_2$—, —O—$CH(CH_3)$—, —S—$CH_2$—, —NH—$C_6H_4$—$CH_2$—; Y is H, —CO—$C_nH_{2n+1}$, —CO—$C_mH_{2m-1}$, —CO—$C_pH_{2p-3}$, —CO—$C_qH_{2q-5}$ (with n=1-22, m=3-22, p=9-22, q=15-22) or —CO-cholesten; Z is H, —$C_nH_{2n+1}$, —$C_mH_{2m-1}$, —$C_pH_{2p-3}$, —$C_qH_{2q-5}$ (with n=1-22, m=3-22, p=9-22, q=15-22); and A is —O— or —NH—.

The present disclosure relates to a copolymer made from a polymerization mixture comprising (a) one or more polymerizable principal monomers, which monomers are characterized as having at least one vinylic group and not containing an amino acid residue, (b) one or more not-functionalized co-principal monomers of formula I and/or formula II wherein Y and Z (formula I) or Z (formula II) are H and A is —O—, (c) one or more functionalized co-principal monomers of formula I and/or formula II wherein Y and Z are not both H (formula I) or Z is not H (formula II), (d) a free radical initiator and, optionally, (e) a chain-transfer-agent.

A particular embodiment of the present disclosure relates to a block copolymer comprising hydrophobic and hydrophilic blocks containing amino acid groups, the block copolymer made by
(a) polymerization of a reaction mixture comprising one or more polymerizable principal monomers not containing an amino acid group, one or more co-principal monomers of formula I and/or formula II with the proviso that at least one of Y and Z is not H, a free radical initiator and optionally a chain-transfer-agent (CTA), the polymerization yielding hydrophobic copolymers and
(b) polymerization of a reaction mixture comprising one or more co-principal monomers of formula I and/or formula II with the proviso that Y and Z are H and A is —O—. a free radical initiator and, optionally, one or more polymerizable principal monomers not containing an amino acid group and a chain-transfer-agent (CTA), the polymerization yielding hydrophilic polymers or copolymers;
whereby the two polymerizations are carried out sequentially, the reaction mixture of the later of the polymerizations further comprising the polymer or copolymer resulting from the earlier polymerization.

The total amount of monomers of formula I and/or formula II in the copolymers and block polymers of this disclosure ranges from 1% to 49.9% (mol) of all monomers contained in the copolymers or block polymers. Preferably, the total amount of monomers of formula I and/or formula II in the latter copolymers and block polymers ranges from 5% to 35% (mol) of all monomers contained in the copolymers or block polymers. Most preferably, the total amount of monomers of formula I and/or formula II in the latter copolymers and block polymers ranges from 5% to 20% (mol) of all monomers.

Typically, the copolymers of this disclosure comprise 0.75-44.9% (mol) not-functionalized co-principal monomers) and 0.25-5% (mol) functionalized co-principal monomer(s). Preferably, they comprise 4.5-32% (mol) not-functionalized co-principal monomers) and 0.5-3% (mol) functionalized co-principal monomer(s). Most preferably, they comprise 4.75-17.75% (mol) not-functionalized co-principal monomers) and 1.25-2.25% (mol) functionalized co-principal monomer(s). The molar ratio of functionalized to not-functionalized co-principal monomers) of this disclosure ranges usually from 1:2 to 1:180. Preferably the molar ratio of functionalized to not-functionalized co-principal monomers) of this disclosure ranges from 1:4 to 1:50. Most preferably the molar ratio of functionalized to not-functionalized co-principal monomers) of this disclosure is in the range of 1:5 to 1:10.

A copolymer or a block copolymer of the present disclosure can be a multiarm copolymer or block copolymer with 3 to 8 linear polymer, copolymer or block copolymer chains. A copolymer or a block copolymer can also have a dendronized structure with 8 to 32 attached linear polymer, copolymer or block copolymer chains.

In particular embodiments of the copolymers and block copolymers of the present disclosure, the principal monomer can be a hydroxyalkyl ester or amide, either N-substituted or unsubstituted, of an alpha-, beta-unsaturated carboxylic acid, a N-vinyl lactam or a 2-acrylamido-2-methylpropane sulfonic acid.

In other embodiments, the principal monomer can be a hydrophobic monomer that is an alkyl, cycloalkyl or aryl acrylate or methacrylate, a mono- or disubstituted itaconate, a styrene or styrene derivative, an acrylonitrile, a vinyl ester, a vinyl ether, an allyl ester, or a fluorine or silicon-containing acrylate or methacrylate.

In further embodiments of the copolymers and block copolymers of the present disclosure, the principal monomer is a combination of two monomers capable of forming a hydrogel, the combinations of monomers selected from the group consisting of hydroxyethylmethacrylate and methyl methacrylate, vinyl pyrrolidone and hydroxyethylmethacrylate, vinyl pyrrolidone and methyl methacrylate, glyceral methacrylate and methyl methacrylate, hydroxyethylmethacrylate or diacetone acyl amide and hydroxyalkyl methacrylates, hydroxyethylmethacrylate or diacetone acyl amide and acrylates with the alkyl groups having from 2 to 6 carbon atoms, hydroxyethylmethacrylate or diacetone acyl amide and vinyl hydroxy acetate, hydroxyethylmethacrylate or diacetone acyl amide and vinyl hydroxy propionate, hydroxyethylmethacrylate or diacetone acyl amide and vinyl hydroxy butyrate, hydroxyethylmethacrylate or diacetone acyl amide and N-vinyl lactams, hydroxyethylmethacrylate or diacetone acyl amide and amino ethyl, N-alkyl amino ethyl or N,N dialkyl amino ethyl methacrylates and acrylates with the alkyl groups having 1 to 2 carbon atoms, hydroxyethylmethacrylate or diacetone acyl amide and hydroxyalkyl vinyl ethers with the alkyl groups having 2 to 4 carbon atoms, hydroxyethylmethacrylate or diacetone acyl amide and 1-vinyloxy 2-hydroxyethylene, hydroxyethylmethacrylate or diacetone acyl amide and 1-vinyloxy 5-hydroxy 3-oxapentane, hydroxyethylmethacrylate or diacetone acyl amide and 1-vinyloxy 8-hydroxy 3,6-dioxaoctane, hydroxyethylmethacrylate or diacetone acyl amide and 1-vinyloxy 14-hydroxy 3,6,9,12 tetraoxatetradectane, hydroxyethylmethacrylate or diacetone acyl amide and N-vinyl morpholine; hydroxyethylmethacrylate or diacetone acyl amide and acrylamide, N-alkyl acrylamide or N,N dialkyl acrylamide with the alkyl groups having 1 to 2 carbons atoms; hydroxyethylmethacrylate or diacetone acyl amide and alkyl vinyl ketone with the alkyl group having 1 to 2 carbon atoms, hydroxyethylmethacrylate or diacetone acyl amide and N-vinyl succinimide or N-vinyl glutarimide, hydroxyethylmethacrylate or diacetone acyl amide and N-vinyl imidazole, and hydroxyethylmethacrylate or diacetone acyl amide and N-vinyl 3-morpholinone.

In other particular embodiments, the principal monomer can be a compound of formula IV

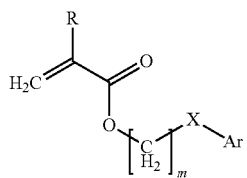

Formula IV wherein:
R is H, $CH_3$, $CH_3$—$CH_2$, $CH_3$—$(CH_2)_2$; m is 0-10; X is nothing, O, S, or NY wherein Y is H, $CH_3$, $C_nH_{2n+1}$ (n=1-10) iso-$C_3H_7$, $C_6H_5$, or $CH_2C_6H_5$; Ar is any aromatic ring, which can be non-substituted or substituted with H, $CH_3$, $C_2H_5$, n-$C_3H_7$, iso-$C_3H_7$, $OCH_3$, $C_6H_{11}$, Cl, Br, $C_6H_5$ or $CH_2C_6H_5$.

In particular, the principal monomer can be 2-ethylphenoxy acrylate, 2-ethylphenoxy methacrylate, 2-ethylthiophenyl acrylate, 2-ethylthiophenyl methacrylate, 2-ethylaminophenyl acrylate, 2-ethylaminophenyl methacrylate, phenyl acrylate, phenyl methacrylate, benzyl acrylate, benzyl methacrylate, 2-phenylethyl acrylate, 2-phenylethyl methacrylate, 3-phenylpropyl acrylate, 3-phenylpropyl methacrylate, 3-propylphenoxy acrylate, 3-propylphenoxy methacrylate, 4-butylphenoxy acrylate, 4-butylphenoxy methacrylate, 4-phenylbutyl acrylate, 4-phenylbutyl methacrylate, 4-methylphenyl acrylate, 4-methylphenyl methacrylate, 4-methylbenzyl acrylate, 4-methylbenzyl methacrylate, 2-2-methylphenylethyl acrylate, 2-2-methylphenylethyl methacrylate, 2-3-methylphenylethyl acrylate, 2-3-methylphenylethyl methacrylate, 2-4-methylphenylethyl acrylate, 2-4-methylphenylethyl methacrylate, 2-(4-propylphenyl)ethyl acrylate, 2-(4-propylphenyl)ethyl methacrylate, 2-(4-(1-methylethyl)phenyl)ethyl acrylate, 2-(4-(1-methylethyl)phenyl)ethyl methacrylate, 2-(4-methoxyphenyl)ethyl acrylate, 2-(4-methoxyphenyl)ethyl methacrylate, 2-(4-cyclohexylphenyl)ethyl acrylate, 2-(4-cyclohexylphenyl)ethyl methacrylate, 2-(2-chlorophenyl)ethyl acrylate, 2-(2-chlorophenyl)ethyl methacrylate, 2-(3-chlorophenyl)ethyl acrylate, 2-(3-chlorophenyl)ethyl methacrylate, 2-(4-chlorophenyl)ethyl acrylate, 2-(4-chlorophenyl)ethyl methacrylate, 2-(4-bromophenyl)ethyl acrylate, 2-(4-bromophenyl)ethyl methacrylate, 2-(3-phenylphenyl)ethyl acrylate, 2-(3-phenylphenyl)ethyl methacrylate, 2-(4-phenylphenyl)ethyl methacrylate, 2-(4-phenylphenyl)ethyl methacrylate, 2-(4-benzylphenyl)ethyl acrylate, or 2-(4-benzylphenyl)ethyl methacrylate. Furthermore, a first principal monomer can be a compound of formula IV and a second principal monomer can be a hydrophilic monomer. In the latter embodiment, the second principal monomer can be 2-hydroxyethyl acrylate, 2-hydroxyethyl methacrylate, 2-N-ethylacrylate pyrrolidone, 2-hydroxy-3-phenoxypropyl acrylate, 2,3-dihydroxypropyl acrylate, 2,3-dihydroxypropyl methacrylate, 2-N-vinyl pyrrolidone, polyethylene oxide:200 monomethyl ether monomethacrylate, polyethylene oxide:200 monomethacrylate, or polyethylene oxide:1000 dimethacrylate.

The present disclosure further relates to a silicone hydrogel contact lens coated with or comprising a copolymer or block copolymer described herein. The copolymer or block copolymer is not covalently bound to the silicon hydrogel lens material and is capable of leaching out from the lens during lens wear and lubricating the lens surfaces. In specific embodiments, the lens surfaces are lubricated for a period of up to 60 days. In other specific embodiments, the lens surfaces are lubricated for a period of at least seven days. In yet other specific embodiments, the lens is a one-day lens, and the copolymer or block copolymer elutes from the lens surfaces during a period of 12-24 hours. In particular embodiments, a silicon hydrogel lens is coated with or comprises a copolymer or block copolymer of the present disclosure that has an average molecular weight of 5,000 Daltons to 120,000 Daltons. In other particular embodiments, at least 80% (w) of the copolymer or block copolymer molecules present in or on a silicone hydrogel contact lens have an average molecular weight of 5,000 Daltons to 120,000 Daltons. In yet other particular embodiments of silicone hydrogel contact lenses that have been coated with or comprise copolymers or block copolymers of this disclosure, the copolymers or block copolymers are present in an amount ranging from 0.1% to 20% (w) of all polymeric material contained in the hydrated lens.

The present disclosure also encompasses a method for preparing a silicone hydrogel contact lens coated with a leachable copolymer or block copolymer described herein. This method comprises the steps of (a) preparing the copolymer or block copolymer and (b) exposing a silicone hydrogel contact lens to an aqueous composition comprising the copolymer or block copolymer of step (a) under conditions under which the copolymer or block copolymer penetrates into the lens. In specific embodiments of this method, the silicone hydrogel contact lens is exposed to an aqueous solution comprising the copolymer or block copolymer for 10-30 min at a temperature of 110-134° C. Typically, the latter aqueous solution comprises the copolymer or block copolymer at a concentration of 0.25-10% (w/v). A method for preparing a silicone hydrogel contact lens in which a copolymer or block copolymer of this disclosure is distributed throughout the lens comprises the steps of (a) preparing the copolymer or block copolymer and (b) polymerizing silicone hydrogel lens-forming material in the presence of the copolymer or block copolymer of step (a). Typically, the copolymer or block copolymer is present in the polymerization reaction of step (b) in an amount not exceeding 20% (w) of all monomers, macromers and polymers.

Also encompassed is a method for regenerating a copolymer- or block copolymer-coated silicon hydrogel contact lens after extended wear, comprising incubating the contact lens in a lens care solution comprising the copolymer or block copolymer with which the lens had originally been coated. Typically, the lens care solution contains between 0.15% (w/v) and 1.5% (w/v) of copolymer or block copolymer.

BRIEF DESCRIPTION OF FIGURES

FIG. 6 Microtribological measurement of friction coefficients of Lotrafilcon B silicone hydrogel lenses (Air Optix Aqua®, Alcon) mock-coated or coated with Cellophil block copolymers MH04. Daily total 1® (DT-1, Alcon) and Air Optix Aqua lenses directly out of their package solution were included as references. Data represent the mean and SD of 10 contact lenses. *Significant according to double-sided t-test ($p=2.97 \times 10^{-5}$); **not significant according to double sided t-test ($p=0.06$).

DETAILED DESCRIPTION OF THE INVENTION

Figure 1:
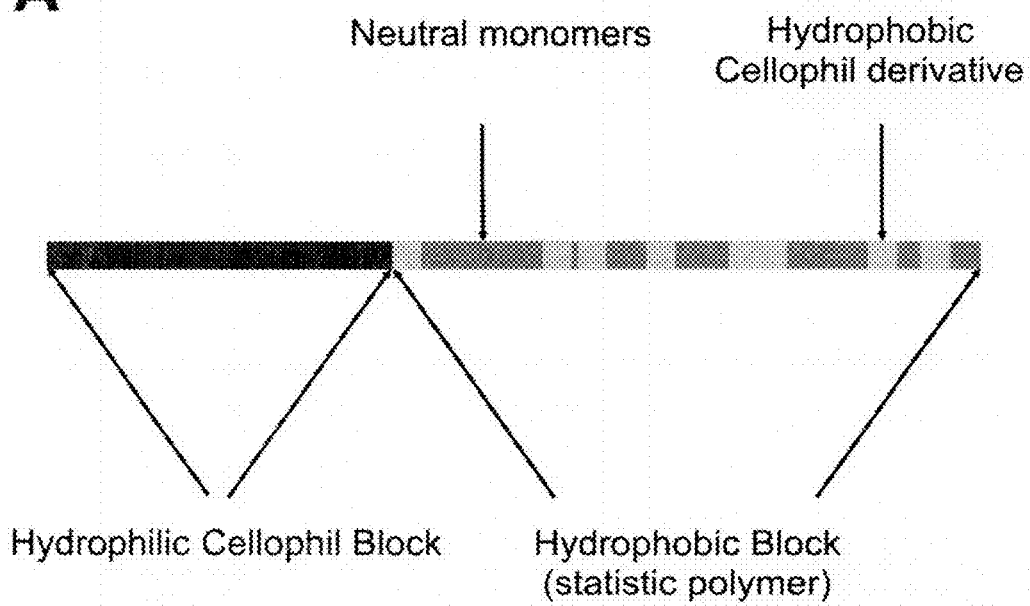
FIG. 1. Cellophil block copolymers containing lipid-like structures. Example structures are represented in panels A and B. Panel C outlines proposed interactions of Cellophil block copolymers and a silicone hydrogel contact lens.
Figure 1:
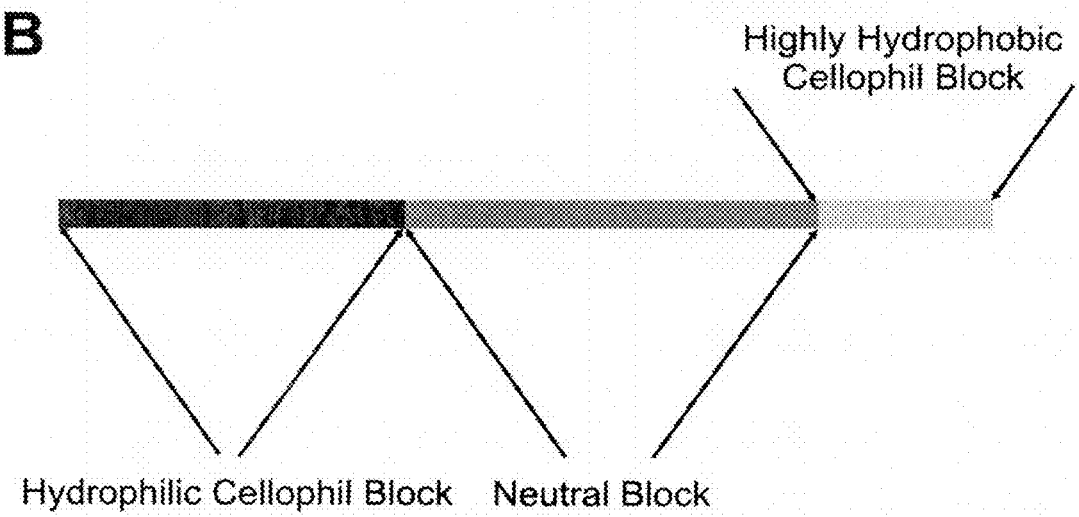
Figure 1:
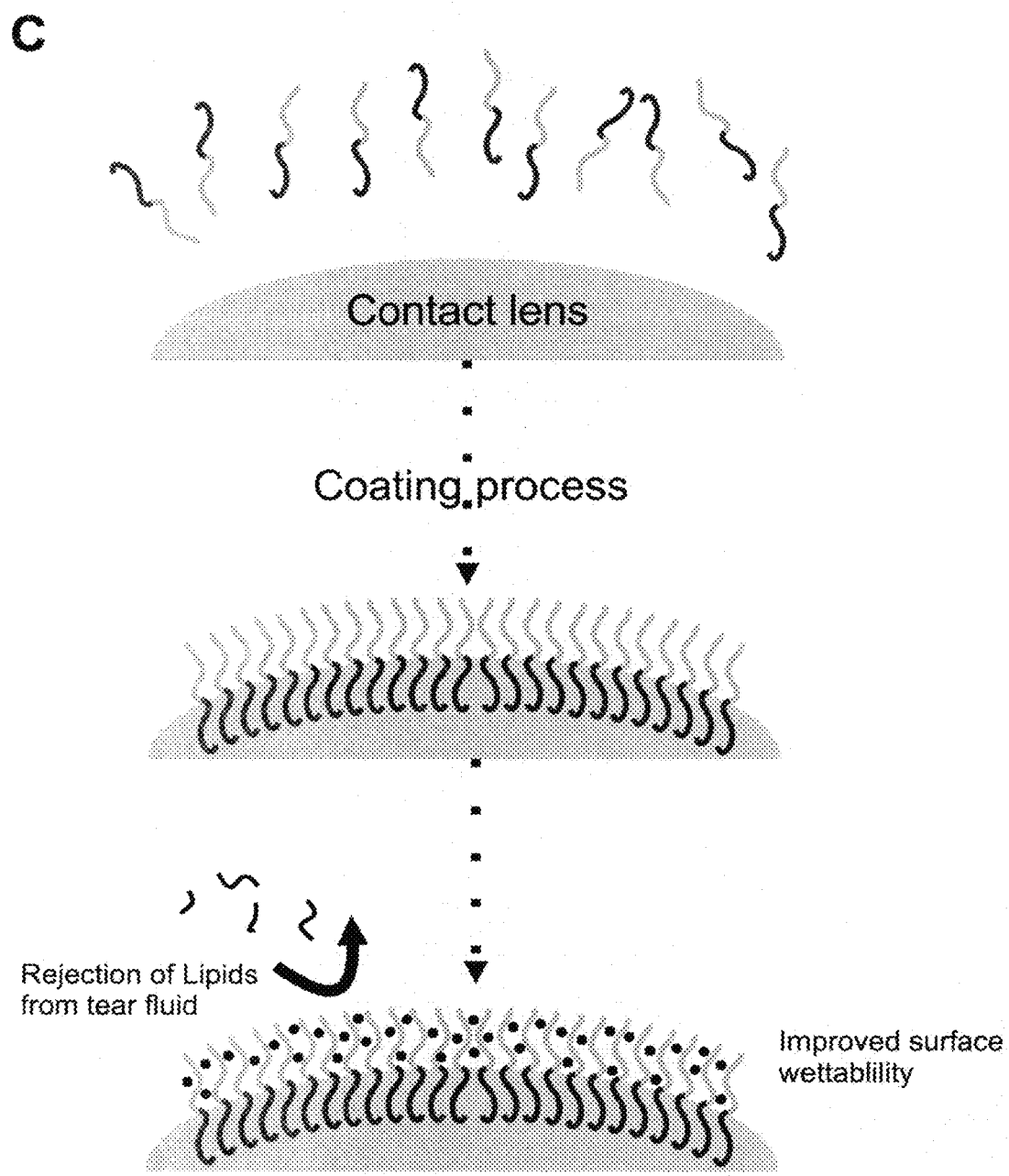

The terms "silicone hydrogel" or "silicone hydrogel material" as used herein refer to a silicone-containing hydrogel obtained by co-polymerization of a polymerizable composition comprising at least one silicone-containing vinylic monomer, silicone-containing macromer or cross-linkable silicone-containing pre-polymer.

A "macromer" refers to a medium and high molecular weight compound or polymer that contains functional groups capable of undergoing further polymerization and/or crosslinking reactions. Medium and high molecular weight typically means average molecular weights greater than 700 Daltons. Preferably, a macromer contains ethylenically unsaturated groups and can be thermally polymerized or photo-polymerized.

A "pre-polymer" refers to a starting polymer which can be cured (e.g., cross-linked and/or polymerized) by radiation, thermally or chemically to obtain a cross-linked and/or polymerized polymer having a molecular weight that is higher than that of the starting polymer.

A "monomer" means a low molecular weight compound that can be polymerized. A "vinylic monomer", as used herein, refers to a low molecular weight compound that has an ethylenically unsaturated group and can be polymerized by radiation or thermally. Low molecular weight typically means a molecular weight of less than 800 Daltons. When referred to in the context of a polymer, the term "monomer" refers to the smallest building blocks of the polymer.

A "hydrogel" refers to a polymeric material that can absorb at least 10 percent by weight of water upon hydration.

In the context of the present disclosure, the term "leachable" is used to characterize the ability of a polymer or copolymer noncovalently present in a lens to diffuse out of the lens material to the interface between lens and tear fluid.

The term "coating" refers to the process of adsorption of polymers or copolymers on a lens surface without a covalent interaction with the lens material. Depending on polymer size, composition and conditions of the coating process, e.g., exposure time, temperature, pressure, etc., a more or less deep penetration into the contact lens may be achieved. Therefore, the term "coating" as used in the context of the present disclosure comprises processes of impregnation as well as of adsorption.

The term "side chain-linked amino acid" means a molecule in which an amino acid is covalently linked through its side chain (e.g., through an ester or amide linkage) to a moiety containing an acryloyl group.

The terms "principal monomer" and "co-principal monomer" are used mainly to facilitate the description of the invention. Principal monomers refer to monomers that do not include an amino acid group, and co-principal monomers refer to monomers that do contain an amino acid group (functionalized or not-functionalized as explained below). Furthermore, the principal monomers (or the single principal monomer) are typically the predominant monomers present in a copolymer of the invention (representing 50% (mol) or more of all monomers present). The co-principal monomers (or the single co-principal monomer) are typically the less prevalent monomers present in a polymer or copolymer of the invention (representing less than 50% (mol) of all monomers present).

A "silicone hydrogel lens-forming material" refers to a polymerizable composition that can be cured (i.e., polymerized and/or cross-linked) thermally, by radiation or chemically to obtain a silicone-containing polymer. Lens-forming materials are well known to a person skilled in the art. In the present disclosure, a silicone hydrogel lens-forming material comprises at least one silicon-containing monomer or macromer. Exemplary silicon hydrogel lens-forming materials include without limitation the reaction mixtures/formulations of lotrafilcon A, lotrafilcon B, etafilcon A, genfilcon A, lenefilcon A, polymacon, acquafilcon A, balafilcon, senofilcon A and comfilcon A. A silicon hydrogel lens-forming material includes in general an initiator (e.g., a photo initiator of the acetophenone type or a thermal initiator of the ammonium peroxide type) to start polymerization and can further include other components, such as a visibility tinting agent, a UV-blocking agent, or a photosensitizer.

Examples of silicone-containing monomers include, without limitation, methacryloxyalkylsiloxanes, 3-methacryloxy propylpentamethyldisiloxane, bis(methacryloxypropyl)tetramethyl-disiloxane, monomethacrylated polydimethylsiloxane, mercapto-terminated polydimethylsiloxane, N-[tris(trimethylsiloxy)silylpropyl]acrylamide, N-[tris(trimethylsiloxy)silylpropyl]methacrylamide, tris(pentamethyldisiloxyanyl)-3-methacrylatopropylsilane (T2), and tristrimethylsilyloxysilylpropyl methacrylate (TRIS). A preferred siloxane-containing monomer is TRIS, which refers to 3-methacryloxypropyltris(trimethylsiloxy) silane, and is represented by CAS No. 17096-07-0. The term "TRIS" also includes dimers of 3-methacryloxypropyltris (trimethylsiloxy) silane.

In addition to a silicon-containing monomer, an initiator and other optional components including a visibility tinting agent, an UV-blocking agent, and a photosensitizer, a silicone hydrogel lens-forming material typically also comprises a hydrophilic vinylic monomer. Among the preferred hydrophilic monomers are N,N-dimethylacrylamide (DMA), 2-hydroxyethylmethacrylate (HEMA), hydroxyethyl acrylate, hydroxypropyl acrylate, hydroxypropyl methacrylate (HPMA), trimethylammonium 2-hydroxy propylmethacrylate hydrochloride, dimethylaminoethyl methacrylate (DMAEMA), dimethylaminoethylmethacrylamide, acrylamide, methacrylamide, allyl alcohol, vinylpyridine, glycerol methacrylate, N-(1,1-dimethyl-3-oxobutyl)acrylamide, N-vinyl-2-pyrrolidone (NVP), acrylic acid and methacrylic acid.

A silicone hydrogel lens-forming material can also comprise a further hydrophobic monomer (in addition to the silicon-containing monomer). By incorporating a further hydrophobic vinylic monomer in a polymerizable fluid composition, the mechanical properties (e.g., modulus of elasticity) of the resultant polymer may be improved. A silicone hydrogel lens-forming material can additionally comprise a leachable wetting agent. A "leachable wetting agent" describes a wetting material that is not covalently attached to the polymer matrix of a silicone hydrogel contact lens and is capable of diffusing to the interface between lens and tear fluid.

The present disclosure relates to a silicone hydrogel contact lens comprising a leachable copolymer comprising monomers) containing not-functionalized side chain-linked amino acids (the amino acids having free alpha-amino- and alpha-carboxyl groups) as well as monomers) containing side chain-linked amino acids that have their alpha-amino groups functionalized with an alkyl- or cholesteryl residue (or aminoalkyl or aminocholesteryl residue) and/or their alpha-carboxyl groups functionalized with an alkyl residue (or aminoalkyl residue) to mimic lipid structures (functionalized side chain-linked amino acids). In a more specific embodiment, the invention relates to a silicone hydrogel contact lens comprising leachable block copolymers containing hydrophilic block(s) comprising not-functionalized side chain-linked amino acids as well as hydrophobic block(s) comprising functionalized side chain-linked amino acids. Silicone hydrogel contact lenses tend to bind proteins and lipids from the tear film during wear [3]. The latter functionalized side chain-linked amino acids are expected to interact with the silicone lens material, resulting in a saturation of the lens surface, which in turn prevents lipid deposition. The not-functionalized side chain-linked amino acids present in the hydrophilic blocks of the block copolymer are expected to face away from the lens surface, enhancing the wettability and lubricity of the lens due to their high capacity for binding water molecules. The so formed aqueous layer improves the lubricity of the lens and functions as an additional barrier against lipid deposition. An illustration of this principle can be found in FIG. 1.

The latter copolymers or block copolymers are also generically referred to herein as Cellophil copolymers or block copolymers, the qualifier "Cellophil" serving to indicate the presence in the materials of side chain-linked amino acids. Amino acids in side chain-linked amino acids include lysine (K), tyrosine (Y), serine (S), threonine (T), cysteine (C), 4-hydroxyproline (HO-P), ornithine (ORN) and 4-amino-phenylalanine (HOX). The amino acids can be the L or the D forms, or racemic mixtures. In the copolymers or block copolymers a single type of side chain-linked amino acid or multiple types of side chain-linked amino acids may be present. For example, a copolymer can comprise both acryloyl-L-lysine (AK) and acryloyl-L-threonine (AT). The amino acid-containing copolymers or block copolymers are not covalently bound to the silicone hydrogel material of a lens, but are dispersed either throughout the lens or within surface proximal regions of the lens and are capable of leaching out from the lens.

Typically, the amino acid-containing copolymers or block copolymers of this disclosure comprise one or more polymerizable principal monomers, which monomers are characterized as having at least one vinylic group (and not containing an amino acid residue), one or more not-functionalized co-principal monomers of formula I or formula II (Y and Z being H, and A being —O—.) and one or more functionalized co-principal monomers of formula I or formula II (Y and Z not being both H (formula I) or Z not being H (formula II)).

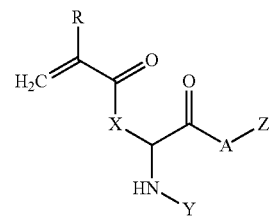

Formula I

Wherein R is —H, —CH$_3$, —CH$_2$—CH$_3$, —(CH$_2$)$_2$—CH$_3$; X is —NH(CH$_2$)$_4$—, —NH(CH$_2$)$_3$—, —O—C$_6$H$_4$—CH$_2$—, —O—CH$_2$—, —O—CH(CH$_3$)—, —S—CH$_2$—, —NH—C$_6$H$_4$—CH$_2$—; Y is H, —CO—C$_n$H$_{2n+1}$, —CO—C$_m$H$_{2m-1}$, —CO—C$_p$H$_{2p-3}$, —CO—C$_q$H$_{2q-5}$ (with n=1-22, m=3-22, p=9-22, q=15-22) or —CO-cholesten and Z is H, —C$_n$H$_{2n+1}$, —C$_m$H$_{2m-1}$, —C$_p$H$_{2p-3}$, —C$_q$H$_{2q-5}$ (with n=1-22, m=3-22, p=9-22, q=15-22); and A is —O— or —NH—

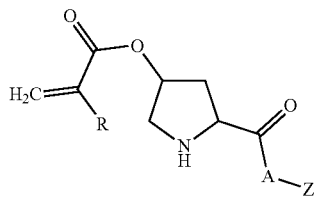

Formula II

Wherein: R is —H, —CH$_3$, —CH$_2$—CH$_3$, —(CH$_2$)$_2$—CH$_3$; Z is H (if A is O), —C$_n$H$_{2n+1}$, —C$_m$H$_{2m-1}$, —C$_p$H$_{2p-3}$, —C$_q$H$_{2q-5}$ (with n=1-22, m=3-22, p=9-22, q=15-22); and A is —O— or —NH—.

Typically, the co-principal monomers are present in a polymerization mixture in an amount between 1% (mol) and 49.9% (mol), more preferably between 5% (mol) and 35% (mol), and most preferably between 5% (mol) and 20% (mol) of total monomers.

The synthesis of not-functionalized side chain-linked amino acids was described previously [13]. Such monomers can be prepared by reacting the amino acid copper complex of lysine, tyrosine, serine, threonine, cysteine or 4-hydroxyproline with either acryloyl chloride, methacryloyl chloride, ethyl-acryloyl chloride or propyl-acryloyl chloride, followed by treatment with a stream of hydrogen sulfide gas or an acidic solution of sodium sulfide to yield the unprotected monomer. In the case of threonine, serine, ornithine and tyrosine, optimized synthesis protocols were generated during the development of the present invention. Furthermore, a novel route for the synthesis of a non-canonical side chain-activated amino acid (containing 4-amino-phenylalanine) was established. All protocols are disclosed under Examples. The synthesis of functionalized side chain-linked amino acids is also described in Examples.

Copolymers comprising two or more types of co-principal monomers of formula I and/or formula II and one or more types of principal monomers typically are prepared in suitable solvents, the choice of solvent depending on the solubility of the respective monomers. A polymerization mixture comprising principal and co-principal monomers, and a free-radical initiator will also include a chain-transfer-agent (CTA) if a controlled radical polymerization technique is used. The mixture is then poured into a suitable container or mold, wherein polymerization is induced. Initiators can be thermal initiators, redox initiators or photo initiators. Typical thermal free radical initiators include peroxides, such as benzophenone peroxide, peroxycarbonates such as bis-(4-t-butylcyclohexyl) peroxydicarbonate, or azonitriles such as azobisisobutyronitrile. A preferred thermal initiator is bis-(4-t-butylcyclohexyl) peroxydicarbonate. Suitable redox initiators for polymerization in aqueous solution are peroxides, e.g., ammonium persulfate, which are destabilized by reaction with a catalyst, e.g., tetramethylethylendiamine (TMDEA or TEMED). Alternatively, the monomers can be photo-polymerized in a container or mold that is transparent to radiation of a wavelength capable of initiating polymerization of the acrylic monomers. A photoinitiator compound, e.g., a benzophenone-type photoinitiator, can also be introduced to facilitate polymerization. Photosensitizers can be introduced as well to permit the use of longer wavelengths. Depending on the initiator compound used, polymerization is initiated by heating, radiation or addition of a catalyst.

In some embodiments it may be necessary to protect the alpha-amino group of an amino acid during synthesis of the corresponding side chain-linked amino acid, e.g., if strong nucleophiles interfere with a polymerization method or subsequent polymer analog modifications. The term "polymer analog modification" in the context of these embodiments means a reaction that takes place along the polymer chain to convert a certain chemical functionality without altering the degree of polymerization of the original polymer. The removal of a protective group is also understood as a polymer analog modification.

Preferred protective groups are fluorenylmethoxycarbonyl (FMOC) and tert-butyloxycarbonyl (BOC) which groups can be removed after polymerization by deprotection in dimethylformamide and piperidine (8:1) [FMOC] or trifluoroacetic acid (TFA) [BOC], respectively. Other suitable protective groups for the α-amino group in co-principal monomers in these embodiments include but are not limited to (Cbz) [carboxybenzyl], Moz [p-methoxybenzylcarbonyl], Bsmoc [1,1-dioxobenzo[b]thiophene-2-methoxycarbonyl].

As the copolymers of this disclosure are intended to be introduced into contact lenses, it is generally preferable to purify the copolymers after polymerization. This step removes potentially harmful ingredients including residual initiators, monomers or catalysts, that could otherwise leach out from a copolymer-containing lens into the eye and surrounding tissues of a lens wearer. Preferred purification methods for copolymers of this invention are dialysis, capillary ultrafiltration or repeated precipitation with subsequent dissolution in a pure solvent.

It is important that a copolymer or block copolymer of this disclosure has a narrow size distribution because the rate of release from a contact lens depends on the size of the copolymer or block copolymer. To obtain a narrow size distribution, the number of free radicals in the polymerization process has to be controlled. This can be achieved by the use of polymerization techniques including atom transfer radial polymerization (ATRP), nitroxide-mediated polymerization (NMP) or reversible addition-fragmentation-chain transfer polymerization (RAFT polymerization). RAFT is the most preferred technique for the copolymers described herein as it is compatible with a broad spectrum of monomers, especially acrylics, and can be performed in aqueous systems. Furthermore, RAFT polymerization can be used for the generation of block copolymers. The RAFT technology was invented by a research group of the Commonwealth Scientific and Industrial Research Organization (CSIRO) in 1998 [14]. Control of polymerization is achieved via chain transfer reactions from the growing polymer chain to a chain transfer agent. This so-called RAFT agent forms an intermediate and is able to fragment into a radical on the propagating chain and another RAFT agent. As a consequence, the number of radicals is limited and all growing polymer chains have a similar likelihood of propagation, resulting in copolymers with a narrow size distribution. Typical polydispersion indices (PDIs) [Đ$_M$=M$_w$/M$_n$, where M$_w$ is the weight-average molar mass and M$_n$ is the number-average molar mass of the polymer] obtained in RAFT polymerizations are in the range of 1.05 to 1.4.

Figure 2:
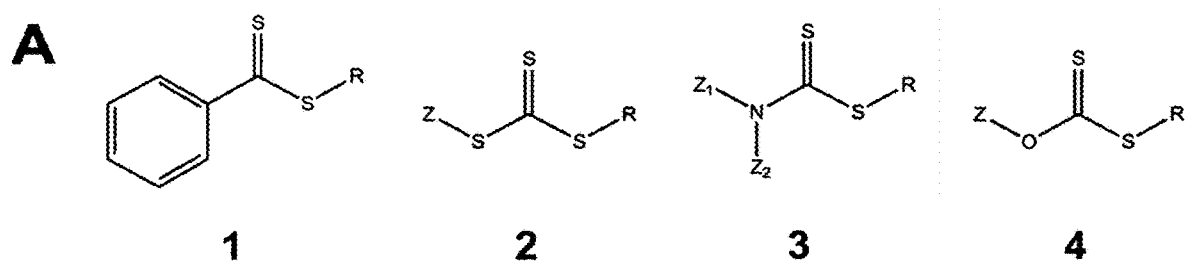
FIG. 2. A: General formulas of RAFT-reagents. The four main classes of thiocarbonylthio-based chain transfer agents are shown in 1-4. B: Gel permeation chromatography (GPC) measurements of N,N-Dimethylacrylamide/acryloyl-L-lysine (DMA/AK) copolymers with different average molecular weights (Mw) synthesized by RAFT polymerization.
Figure 2:
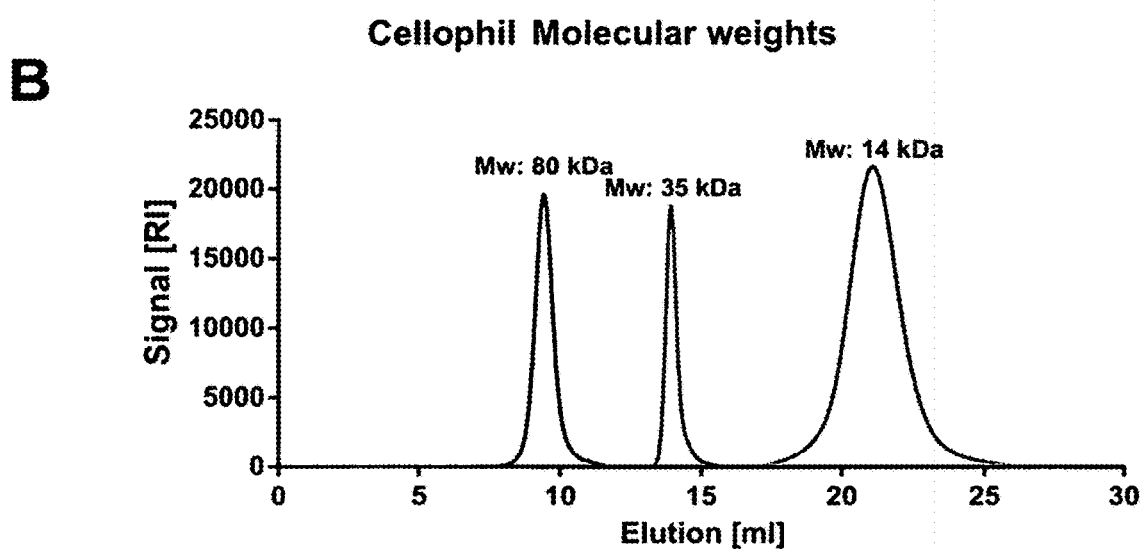

Suitable chain transfer agents for RAFT polymerizations of copolymers as disclosed herein are thiocarbonylthio compounds. Thiocarbonylthio compounds can be divided into four main classes, i.e., dithiobenzoates, trithiocarbonates, dithiocarbamates, and xanthates (FIG. 2). RAFT polymerization is especially useful for the synthesis of well-defined block copolymers of this invention. After consumption of all monomers in a reaction mixture, each polymer chain still contains an active chain-transfer agent (CTA) group. These active polymer chains can therefore be defined as macro-CTAs. If new monomers and initiators are added to the reaction mixture, polymerization is reinitiated, resulting in the addition of a second polymeric block. This stepwise process can be repeated until the desired polymer architecture is attained. Typically, a reaction mixture is purified before addition of a second monomer species (or a second set of monomer species) because by-products of the preceding polymerization reaction could interfere with the subsequent polymerization process. Common purification methods for copolymers/macro-CTAs include but are not limited to dialysis, capillary ultrafiltration, precipitation and preparative gel permeation chromatography.

Depending on their intended use, copolymers of this disclosure can have different architectures, e.g., they can be linear copolymers (statistically co-polymerized or block co-polymerized) or multiarm copolymers. These multiarm or star-shaped Cellophil copolymers in which a single branch point gives rise to multiple linear polymer/copolymer chains or arms, respectively, have different viscoelastic properties (e.g., have often lower viscosities) than linear copolymers of the same size. Depending on the core structure, the number of linear polymer/copolymer arms is usually in the range of 3 to 8. Dentronized copolymers or dentrimers can contain far higher numbers of arms. These copolymer architectures can be obtained by two different synthesis routes, an arm-first approach where linear Cellophil copolymers are synthesized first and are subsequently coupled to a core structure or a core-first approach were linear polymer/copolymer chains are grown directly on a precursor structure, e.g., a core with attached RAFT agents.

Co-principal monomers of formula I or II are co-polymerized with one or more principal monomers. Hydrophilic principal monomers include, for example, the hydroxyalkyl esters and amides, both N-substituted and unsubstituted, of alpha-, beta-unsaturated carboxylic acids (e.g., N-isopropylacrylamide), N-vinyl lactams and 2-acrylamido-2-methyl-propane sulfonic acid. The alpha-, beta-unsaturated acids useful in this invention are acrylic acid, crotonic acid, methacrylic acid, itaconic acid, maleic acid, maleic anhydride, or fumaric acid. The poly-functional alcohols which form the hydroxyalkyl esters include glycol, glycerol, propylene glycol, trimethylene glycol and other polyhydric alkanols, dialkylene glycols of 2 to 12 carbon atoms, and polyalkylene glycols. Polyalkylene glycols are exemplified by triethylene glycol, tetraethylene glycol, pentaethylene glycol, and hexaethylene glycol. Preferred hydrophilic monomers include the hydroxyalkyl esters, specifically hydroxyethyl methacrylate (HEMA). Suitable hydrophobic principal monomers include cycloalkyl ester, tertiary-butyl styrene, polycyclic acrylate or methacrylate as well as mixtures thereof. More particularly, the polycyclic acrylics can be isobornyl acrylate, isobornyl methacrylate, dicyclopentanedienyl acrylate, dicyclopentanedienyl methacrylate, adamantyl acrylate, adamantyl methacrylate, isopinocamphyl acrylate, isopinocamphyl methacrylate, etc., and mixtures thereof. Cycloalkyl ester monomer is of formula Ill below (Formula I from U.S. Pat. No. 4,668,506). Illustrative of these cycloalkyl esters are menthyl methacrylate, menthyl acrylate, tertiary-butyl cyclohexyl methacrylate, isohexyl cyclopentyl acrylate, and methylisopentyl cyclooctyl acrylate.

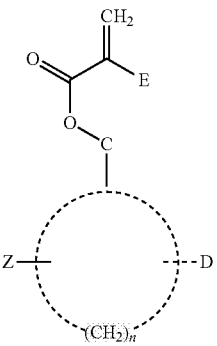

Formula III wherein: D is branched or normal alkyl of 3 to 6 carbon atoms, E is H or $CH_3$, Z is H or $CH_3$, and n is an integer from 3 to 8.

Other well-known hydrophobic monomers may be used as principal monomers in the formulation of copolymers of this disclosure, including monomers containing at least one silicone or fluorine atom as a part of their composition. Hydrophobic monomers include alkyl (chain length 2 to 22 carbon atoms), cyclo-alkyl and aryl acrylates and methacrylates as well as mono- or disubstituted itaconates, styrene and its derivatives, acrylonitrile, vinyl esters such as vinyl acetate or vinyl pentacetyl gluconate, vinyl ethers such as vinyl butyl ether, allyl esters such as allyl acetate, propionate or butyrate, fluorine containing monomers such as octafluoropentyl methacrylate and silicone-containing monomer, e.g., 1,1,1-tris(trimethoxysiloxy)-3-methacryloxy propylsilane or heptamethyltrisiloxanyl ethyl acrylate.

Preferably, the amino acid-containing copolymers of this disclosure will have a water content that is higher than that of the silicone hydrogel lens material into which they are introduced or which they coat. More preferably, their water content is between 30% and 90%, and most preferably between 50% and 80%.

Suitable combinations of principal monomers that may be co-polymerized in the presence of co-principal monomers of formula I and/or formula II to produce hydrogel copolymers comprise hydroxyethylmethacrylate and methyl methacrylate, vinyl pyrrolidone and hydroxyethylmethacrylate or methyl methacrylate; glyceral methacrylate and methyl methacrylate; hydroxyethylmethacrylate/diacetone acyl amide and hydroxyalkyl methacrylates, acrylates with the alkyl groups composed of 2 to 22 carbon atoms; vinyl hydroxy acetate, vinyl hydroxy propionate, vinyl hydroxy butyrate; N-vinyl lactams namely N-vinyl pyrrolidone, N-vinyl caprolactam and N-vinyl piperidone; amino ethyl, N-alkyl amino ethyl or N,N dialkyl amino ethyl methacrylates and acrylates with the alkyl groups having 1 to 2 carbon atoms; hydroxyalkyl vinyl ethers with the alkyl groups having 2 to 4 carbon atoms; 1-vinyloxy 2-hydroxyethylene, 1-vinyloxy 5-hydroxy 3-oxapentane, 1-vinyloxy 8-hydroxy 3,6-dioxaoctane, 1-vinyloxy 14-hydroxy 3,6,9,12 tetraoxatetradecane; N-vinyl morpholine; acrylamide, N-alkyl acrylamide or N,N dialkyl acrylamide with the alkyl groups having 1 to 2 carbons atoms; alkyl vinyl ketone with the alkyl group having 1 to 2 carbon atoms; N-vinyl succinimide and N-vinyl glutarimide; N-vinyl imidazole; and N-vinyl 3-morpholinone.

Also suitable for introduction into silicone hydrogel lens-forming material or for coating of a lens formed from such material are copolymers of monomers of formula I and/or formula II (of which at least one is a not-functionalized co-principal monomer and another is a functionalized co-principal monomer), and hydroxyethylmethacrylate and methylmethacrylate. In other copolymers the combination of hydroxyethylmethacrylate and methylmethacrylate may be substituted by vinyl pyrrolidone and hydroxyethylmethacrylate or methyl methacrylate; glyceral methacrylate and methyl methacrylate; hydroxyethylmethacrylate/diacetone acyl amide and various other monomers such as hydroxyalkyl methacrylates and acrylates with the alkyl groups having from 2 to 6 carbon atoms; vinyl hydroxy acetate, vinyl hydroxy propionate, vinyl hydroxy butyrate; N-vinyl lactams namely N-vinyl pyrrolidone, N-vinyl caprolactam and N-vinyl piperidone; amino ethyl, N-alkyl amino ethyl or N,N-dialkyl amino ethyl methacrylates and acrylates with the alkyl groups having 1 to 2 carbon atoms; hydroxyalkyl vinyl ethers with the alkyl groups having 2 to 4 carbon atoms; 1-vinyloxy 2-hydroxyethylene, 1-vinyloxy 5-hydroxy 3-oxapentane, 1-vinyloxy 8-hydroxy 3,6-dioxaoctane, 1-vinyloxy 14-hydroxy 3,6,9,12 tetraoxatetradectane; N-vinyl morpholine; acrylamide, N-alkyl acrylamide or N,N dialkyl acrylamide with the alkyl groups having 1 to 2 carbons atoms; alkyl vinyl ketone with the alkyl group having 1 to 2 carbon atoms; N-vinyl succinimide and N-vinyl glutarimide; N-vinyl imidazole; and N-vinyl 3-morpholinone.

Other (hydrogel) copolymers of the invention can be prepared by co-polymerization of co-principal monomers of formula I and/or formula II (of which at least one is a not-functionalized co-principal monomer and another is a functionalized co-principal monomer) and one or more principal monomers of formula IV:

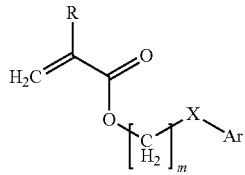

Formula IV wherein:
R is H, $CH_3$, $CH_3$—$CH_2$, $CH_3$—$(CH_2)_2$; m is 0-10; X is nothing, O, S, or NY wherein Y is H, $CH_3$, $C_nH_{2n+1}$ (n=1-10) iso-$C_3H_7$, $C_6H_5$, or $CH_2C_6H_5$; Ar is any aromatic ring, such as benzene, which can be non-substituted or substituted with H, $CH_3$, $C_2H_5$, n-$C_3H_7$, iso-$C_3H_7$, $OCH_3$, $C_6H_{11}$, Cl, Br, $C_6H_5$ or $CH_2C_6H_5$.

Suitable monomers of formula IV include, but are not limited to 2-ethylphenoxy methacrylate, 2-ethylthiophenyl methacrylate, 2-ethylaminophenyl methacrylate, phenyl methacrylate, benzyl methacrylate, 2-phenylethyl methacrylate, 3-phenylpropyl methacrylate, 3-propylphenoxy methacrylate, 4-butylphenoxy methacrylate, 4-phenylbutyl methacrylate, 4-methylphenyl methacrylate, 4-methylbenzyl methacrylate, 2-2-methylphenylethyl methacrylate, 2-3-methylphenylethyl methacrylate, 2-4-methylphenylethyl methacrylate, 2-(4-propylphenyl)ethyl methacrylate, 2-(4-(1-methylethyl)phenyl)ethyl methacrylate, 2-(4-methoxyphenyl)ethylmethacrylate, 2-(4-cyclohexylphenyl)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate), 2-(4-benzylphenyl)ethyl methacrylate, and the corresponding acrylates. More suitable may be copolymers that comprise at least two monomers of formula I and/or formula II (of which at least one is a not-functionalized co-principal monomer and another is a functionalized co-principal monomer), at least one monomer of formula IV, and a hydrophilic monomer. Suitable hydrophilic monomers include 2-hydroxyethyl acrylate; 2-hydroxyethyl methacrylate; 2-N-ethylacrylate pyrrolidone; 2-hydroxy-3-phenoxypropyl acrylate; 2,3-dihydroxypropyl acrylate; 2,3-dihydroxypropyl methacrylate; 2-N-vinyl pyrrolidone; polyethylene oxide:200 monomethyl ether monomethacrylate; polyethylene oxide:200 monomethacrylate; polyethylene oxide:1000 dimethacrylate. Preferred hydrophilic monomers for use in the present invention are include 2-hydroxyethyl acrylate; 2-hydroxyethyl methacrylate; and polyethylene oxide:1000 dimethacrylate.

A copolymer of the invention can be introduced into polymerized silicone hydrogel material or a lens formed from such material by exposure of the polymerized material or lens to a solution/suspension containing a copolymer of the invention (coating). To increase efficiency, the latter exposure typically occurs at an elevated temperature for an adequate period of time. Typical procedures involve autoclaving at 110-134° C. for about 10-30 minutes followed or not by a post-incubation at a lower temperature. Alternatively, the copolymer of the invention can be introduced in silicone hydrogel lens-forming material during polymerization, i.e., the copolymer of the invention (that does not contain any reactive bonds or groups) can be a component of the silicone hydrogel lens-forming reaction mixture.

The so-loaded silicone hydrogel contact lens will elute or leach amino acid-containing copolymer (or block copolymer) at a rate that keeps the front and back surfaces of the lens lubricated during the intended period of wear of the lens. In order to extend the period of functionality of the copolymers or block copolymers of this disclosure, e.g., in case of lenses with wear periods of several weeks to months, it may be useful to re-coat a silicone hydrogel lens with fresh copolymer or block-copolymer. This can be achieved by incubation, usually overnight, of the lens in a lens care solution containing a small percentage (e.g., 0.15-1.5% (w/v)) of the copolymer or block copolymer of the invention.

The lubricating effect as well as the length of time during which a lubricating effect can be maintained in the eye of a wearer depends on several factors which include the molecular weight of the amino acid-containing copolymer, the concentration of the amino acid-containing copolymer in the lens (or region of the lens), the distribution of the amino acid-containing copolymer in the lens, and the composition of the amino acid-containing copolymers. Regarding the composition of an amino acid-containing copolymer, of consequence are both the level and the nature of co-principal monomers present as well as the nature of the principal monomer(s). The latter parameters are optimized for a lens of interest.

To arrive at a desired level of lubricity that persists for the intended duration of wear of a lens, the afore-mentioned parameters are systematically varied until the desired result is obtained. Typically, experimental lenses will be tested initially in vitro and subsequently in animal and human subjects. In vitro methods include methods for measuring wettability. A measure of wettability is the contact angle that can be determined by several methods, including the sessile drop technique, the captive bubble technique or the Wilhelmy balance method [1, 15].

A more direct approach to measuring lubricity involves assessment of friction of hydrogel contact lenses, from which assessment lubricity can be derived [16]. Methods for measuring friction and lubricity of hydrogel contact lenses were described, e.g. in [17].

It is noted that defining useful parameter values typically does not require undue effort both because the number of parameters is limited and preferred ranges of some parametric values are known. The level of co-principal monomers in an amino acid-containing copolymer will preferably be between 5% (mol) and 35% (mol), and most preferably between 5% (mol) and 20% (mol), of all monomers present in the polymerization mixture. The average molecular weight of the amino acid-containing copolymer will generally be between 5,000 and 120,000 Daltons, preferably between 5,000 and 30,000 Da, and most preferably between 5,000 and 12,000 Da.

EXAMPLES

Note: In the examples relating to synthesis of side chain-linked amino acids names are first given in UPAC nomenclature. Thereafter, abbreviated names are used. Table 1 shows the correspondence.

TABLE 1

UPAC names and abbreviations

| UPAC | Abbreviation |
| --- | --- |
| (S)-6-acrylamido-2-aminohexanoic acid | Acryloyl-L-lysine, AK |
| (2S)-3-(acryloyloxy)-2-aminopropanoic acid | Acryloyl-L-serine, AS |
| (2S)-3-(acryloyloxy)-2-aminobutanoic acid | Acryloyl-L-threonine, AT |
| (S)-3-(4-(acryloyloxy)phenyl)-2-aminopropanoic acid | Acryloyl-L-tyrosine, AY |
| (S)-2-(4-acrylamidophenyl)-2-aminoacetic acid | Acryloyl-L-amino-phenylalanine, AHOX |
| (2S)-4-(acryloyloxy)pyrrolidine-2-carboxylic acid | Acryloyl-L-cysteine, AC |
| (R)-3-(acryloylthio)-2-aminopropanoic acid | Acryloyl-L-oxi-proline, AHOP |
| (S)-6-acrylamido-2-palmitamidohexanoic acid | Nε-acryloyl-Nα-palmityl-L-Lysine, AK-PAL |
| (S)-6-acrylamido-2-dodecanamidohexanoic acid | Nε-acryloyl-Nα-lauryl-L-Lysine, AK-LAU |
| (S,E)-6-acrylamido-2-octadec-9-enamidohexanoic acid | Nε-acryloyl-Nα-oelityl-L-Lysine, AK-OEL |
| (2R)-6-acrylamido-2-(10,13-dimethyl-17-(6-methylheptan-2-yl)-2,3,4,7,8,9,10,11,12,13,14,15,16,17-tetradecahydro-1H-cyclopenta[a]phenanthrene-3-carboxannido)hexanoic acid | Nε-acryloyl-Nα-cholesten-3β-carboxyl-L-Lysine, AK-CHOL |
| (S)-methyl-6-acrylamido-2-dodecanamidohexanoate | Nε-acryloyl-Nα-lauryl-L-Lysine-methylester, MEO-AK-LAU |

Example 1: Synthesis of (S)-6-acrylamido-2-aminohexanoic Acid Monomers Via Copper Complex L-lysine (14.62 g; 100 mmol) was dissolved in 150 ml deionized water and heated to about 80° C. Copper carbonate (16.6 g; 75 mmol) was added in portions over a period of 30 minutes. The reaction was stirred for an additional 30 minutes. The hot, deep-blue suspension was filtered through silica gel. The filter was washed with a small amount of water. On the subsequent day, the lysine copper complex-containing the combined filtrate was cooled in an ice bath, and 100 ml tetrahydrofuran (THF) were added. A solution of acryloyl chloride in methyl-tert-butylether (TBME) (8.9 ml, 110 mmol) was added dropwise during a period of one hour. The pH was initially maintained between 8 and 10 by parallel, dropwise addition of 10% sodium hydroxide solution. After half of the acryloyl chloride solution had been added, product began to precipitate. When most of the acryloyl chloride had been added, addition of sodium hydroxide was slowed down to allow the pH to drop to about 6 and the temperature of the reaction mixture was allowed to reach room temperature. The blue suspension was stirred during an additional 2 hours and was then filtered. The solid material retained on the filter was washed with water and acetone and then dried. A yield of 6.5 g of acryloyl-L-lysine copper complex was obtained.

Acryloyl-L-lysine copper complex (29.5 g) was suspended in 300 ml deionized water and cooled in an ice bath. $H_2S$ gas was bubbled into the suspension until copper sulfide precipitation was complete. Three grams of active charcoal were added to the suspension. The suspension was heated briefly to 100° C. After cooling to room temperature, 500 ml acetone was added to the suspension which was then filtered on silica gel. The clear filtrate was put in a rotary evaporator. After evaporation of the solvent, the solid product was recrystallized from 200 ml of 50% aqueous acetone. A yield of 17.76 g (69.76%) of white powder was obtained. The structure of the compound was verified by NMR and LC-MS spectroscopy.

Example 2: Synthesis (2S)-3-(acryloyloxy)-2-aminopropanoic Acid

A solution of L-serine (5 g, 47.6 mmol) in water (50 ml) was heated to 80° C., and solid copper carbonate (5.79 g, 26.2 mmol) was added. The solution was stirred for 10 min. Undissolved residue was subsequently collected by filtration and washed with water (30 ml). The combined filtrate was cooled in an ice bath, and KOH (27.1 ml, 47.6 mmol) was added slowly. To this solution a mixture of acryloyl chloride (4.52 ml, 59.5 mmol) in acetone (30 ml) was added dropwise. The reaction mixture was then incubated at 4° C. overnight under stirring. The formed solid was isolated and washed with water (50 ml)/methanol (50 ml)/ethyl-tert-butylether (50 ml) (MTBE) and finally dried under reduced pressure to give O-acryloyl-l-serine-$Cu^{2+}$ complex (3.8 g, 10.01 mmol; 42.1% yield). The copper in the complex was subsequently removed by a similar procedure as that described in example 1. A yield of 1.43 g (45%) of acryloyl-L-serine as white powder was obtained. The identity of the compound was verified by NMR and LC-MS spectroscopy.

Example 3: Synthesis (2S)-3-(acryloyloxy)-2-aminobutanoic Acid

A reaction vessel with 6 ml trifluoroacetic acid (TFA) was cooled in an ice bath. Subsequently, solid L-threonine (2.00 g, 16.79 mmol) was added, and the mixture was stirred for 5 min. Trifluromethanesulfonic acid (0.18 ml, 2.0 mmol) and, subsequently, acryloyl chloride (2.5 ml, 32.9 mmol) were added, and the reaction mixture was incubated for 2 h at room temperature. After completion of the reaction, the product was precipitated with methyl-tert-butylether (MTBE). After isolation of the solid, the product was washed with MTBE and acetone. O-Acryloyl-L-threonine hydrochloride was finally dried under reduced pressure to give a white powder (yield 32.4%). The structure of the compound was verified by NMR and LC-MS spectroscopy.

Example 4: Synthesis of (S)-3-(4-(acryloyloxy)phenyl)-2-aminopropanoic Acid

The synthesis of O-acryloyl-L-tyrosine-$Cu^{2+}$-complex was performed according to the procedure described in Example 1. Copper was removed from the complex by the following procedure: 73.15 g (140 mmol) of O-acryloyl-L-tyrosine-$Cu^{2+}$-complex was dissolved in 220 ml 2 N HCL in a grinding dish. The mixture was homogenized using Polytron® PT 3000 equipment. Subsequently, the mixture was filtered and the residue washed twice with 50 ml 2 N HCL. The solid compound was then dried over NaOH at 40° C. under reduced pressure to give O-acryloyl-L-tyrosine hydrochloride (46.96 g, 63% yield).

Example 5: Synthesis of (S)-2-(4-acrylamidophenyl)-2-aminoacetic Acid

Boc-4-amino-L-phenylalanine (2.50 g, 8.9 mmol, Anaspec, Fremont, Calif.) was dissolved in 25 ml chloroform. Triethylamine (2.47 ml, 17.8 mmol) was given to this solution, and the mixture was cooled to −15° C. Subsequently, acryloyl chloride (0.79 ml, 9.8 mmol) in chloroform was added dropwise to the mixture under stirring. After acryloyl chloride addition was completed, the reaction mixture was stirred for three additional hours. The reaction mixture was thereafter passed through a glass filter, the protected (S)-2-(4-acrylamidophenyl)-2-aminoacetic acid was purified by column chromatography, and residual solvents were evaporated. The protected (S)-2-(4-acrylamidophenyl)-2-aminoacetic acid (500 mg, 1.5 mmol) was dissolved in 5 ml dichloromethane (DCM). Trifluoracetic acid (TFA) (800 µl, 10.38 mmol) was added, and the solution was stirred for 1 h at room temperature. Afterwards, the solvent was removed under reduced pressure, 5 ml DCM were added, and solvent was again removed under reduced pressure. This procedure was repeated several times. Finally, the product was dissolved in 3 ml DCM and precipitated with methyl-tert-butylether (MTBE). The solid was collected on a glass filter and dried in vacuo to obtain pure acryloyl-4-amino-L-phenylalanine at a yield of 15%. The structure of the compound was verified by NMR.

Example 6: Synthesis of (2S)-4-(acryloyloxy)pyrrolidine-2-carboxylic acid and (R)-3-(acryloylthio)-2-aminopropanoic Acid Synthesis of these compounds was performed as described in Example 1. For (2S)-4-(acryloyloxy)pyrrolidine-2-carboxylic acid and (R)-3-(acryloylthio)-2-aminopropanoic acid, the starting materials were, respectively, 4-hydroxy-L-proline and L-cysteine.

Example 7: Synthesis of Fmoc-acryloyl-lysine

Acryloyl-L-lysine (10 g) was dissolved in 106 ml of a 10% (w/v) solution of sodium carbonate in water, which solution was diluted with 100 ml dioxane. Fmoc-chloride (14 g) dissolved in 50 ml dioxane was added to the reaction mixture over a period of 30 minutes at 15-25° C. The reaction mixture was stirred for 3 hours at room temperature and then adjusted to pH 2 with 10% aqueous HCl. After extraction with ethyl acetate, the organic phase was evaporated to dryness. The resulting clear yellowish oil (21.4 g) was put on a 200 g silica gel cushion and washed with ethyl acetate. The product was extracted from the silica gel with 3:1 (v/v) ethyl acetate/methanol. After evaporation of the solvent, a white powder (10.4 g, 50% yield) was obtained. The structure of the compound was verified by NMR.

Example 8: Synthesis of Fmoc-acryloyl-L-serine, Fmoc-acryloyl-L-threonine, Fmoc-acryloyl-L-tyrosine, Fmoc-acryloyl-L-oxiproline and Fmoc-acryloyl-L-cysteine Syntheses of these compounds were performed as described in Example 7.

Example 9: Synthesis of Methacryl/Ethylacryl/Propylacryl Derivatives of Alpha-Amino-Protected and Unprotected Amino Acids Syntheses of methacryl/ethylacryl/propylacryl-derivatives were performed using the respective acid chloride, e.g. methacryloyl chloride, under conditions described in Examples 1 to 8.

Example 10: Synthesis of (S)-6-acrylamido-2-palmitamidohexanoic Acid

The following procedure represents a general synthesis route for functionalization of the free alpha amino group in a side chain-linked amino acid with a fatty acid.

Palmitoic acid (5 g, 19.5 mmol) was dissolved in thionyl chloride (2.12 ml, 29.2 mmol). The reaction mixture was heated under reflux until gas formation stopped. Subsequently, the excess thionyl chloride was removed in vacuo to give palmitoyl chloride (5.36 g, 19.50 mmol; 100% yield; yellow oil). Palmitoyl chloride (5.36 g, 19.5 mmol) was then added to a solution of acryloyl-L-lysine (3.90 g, 19.50 mmol) and sodium bicarbonate (3.1 g, 29.3 mol) in a water/THF mixture (5/2, 70 ml). This mixture was incubated overnight under stirring. Nε-acryloyl-Nα-palmityl-L-Lysine was subsequently purified by recrystallization form ethanol/TBME and compound identity was verified by NMR ($^1H$, $^{13}C$)(yield 55%).

Example 11: Synthesis of (S,E)-6-acrylamido-2-octadec-9-enamidohexanoic Acid The same procedure as in examples 10 was used for functionalization of the α-amino group of acryloyl-L-Lysine with oleic acid to produce a model compound that contains an unsaturated fatty acid chain.

Example 12: Synthesis of Nε-acryloyl-Nα-cholesten-3β-carboxyl-L-Lysine

Cholesterol was converted into cholesterol acid by a procedure described in [18]. Cholesterol acid was subsequently used to functionalize the α-amino group of acryloyl-L-Lysine using a protocol as described in example 10.

Example 13: Synthesis of a HEMA/Acryloyl-L-Lysine Copolymer Using Free Radical Polymerization In a 200 ml reaction vessel, 2-hydroxyethylmethacylate (HEMA) (2.6 g, 20 mmol) and acryloyl-L-lysine (4 g, 20 mmol) were dissolved in 100 ml deionized water. The solution was degased in an ultrasonic bath. Ammonium persulfate (APS) (300 mg, 1.43 mmol) and tetramethylethylenediamine (TMEDA) (0.1 ml, 0.66 mmol) were added to the degased solution. Polymerization was performed for 4 h at room temperature and stopped by cooling the reaction vessel to 4° C. The resulting copolymer was purified by extensive dialysis against deionized water using a dialysis tube with a 3.5 kDa molecular weight cut-off (MWCO). The purified copolymer was lyophilized and its molecular weight estimated by gel permeation chromatography (GPC). A detailed description of this method is presented in Example 14.

Example 14: Synthesis of DMA/Acryloyl-L-Lysine Copolymers of Different Sizes Using RAFT Polymerization N,N-Dimethylacrylamide (DMA) (0.312 ml, 3.03 mmol) and acryloyl-L-lysine (67 mg, 0.336 mmol) were dissolved in 15 ml deionized water containing water-soluble RAFT agent (2-(ethylthiocarbonothioylthio)-2-methylpropanoic acid) (7.62 mg, 34 μmol, molar ratio of RAFT agent to monomers: 1:100). The mixture was degased using an ultrasonic bath. Polymerization was started by the addition of 2,2 azobis(2-(2-imidazolin-2-yl)) di-hydrochloride (initiator molar amount of 1/5 of that of the RAFT agent; 2.2 mg, 6.8 μmol) and subsequent heating to 45° C., which temperature was maintained for 6 h. The resulting copolymer was purified by extensive dialysis against deionized water using a dialysis membrane with a 3.5 kDa MWCO. The purified copolymer was finally lyophilized. It is noted that the molecular size of the copolymer was a function of the ratio of RAFT agent to monomers. A molar ratio of 1:100 resulted in a 14 kDa copolymer, a molar ratio of 1:250 in a 35 kDa copolymer and a molar ratio of 1:600 in an 80 kDa copolymer. Molecular weights of copolymers were verified by gel permeation chromatography (GPC). For GPC analysis a stock solution of 3.33 mg/ml copolymer was prepared in elution buffer (deionized water containing 0.05% (w/v) $NaN_3$) and filtered through a 0.45 μm syringe filter. Subsequently, 0.4 ml of stock solution was injected in the port of the GPC device (1260 Infinity LC-System, Agilent, Santa Clara, Calif.). Chromatography was performed at a constant flow rate of 0.5 ml/min in elution buffer. Copolymer samples were separated on a Suprema three-column system (pre-column, 1000 Å, 30 Å; 5 μm particle size; PSS, Mainz, Germany) which was placed in an external column oven at 55° C. Copolymers were analyzed by RI (refractive index) and UV detectors. A calibration curve (10 points) was established using a pullulan standard. Molecular weights of characterized copolymers were estimated with reference to this standard. An exemplary chromatogram of a mixture of DMA/acryloyl-L-lysine copolymers of different molecular weights is presented in FIG. 2B.

Figure 3:
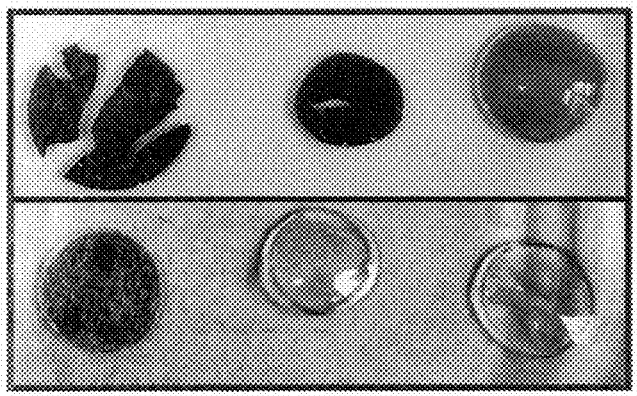
FIG. 3. Interactions tests of Cellophil copolymers with silicone hydrogel contact lenses A: Elution of different Cellophils from a lens. Visual representation of the time course of release of copolymers from HEMA-based silicone hydrogel contact lenses that had been coated with different Cellophil copolymers. Copolymers are stained with ninhydrine. B-D: Ninhydrine staining of cross sections of HEMA-based silicone hydrogel contact lenses. The lens in B had not been coated, and the lenses in C and D had been coated with a Cellophil (HEMA) copolymer and a Cellophil (NIPAAm) copolymer, respectively.
Figure 3:
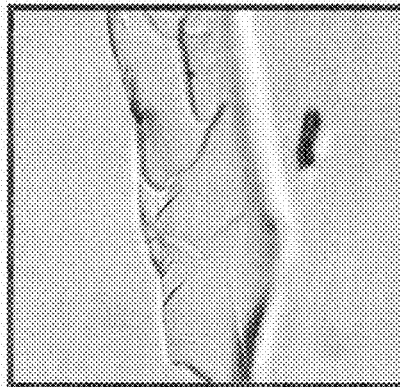
Figure 3:
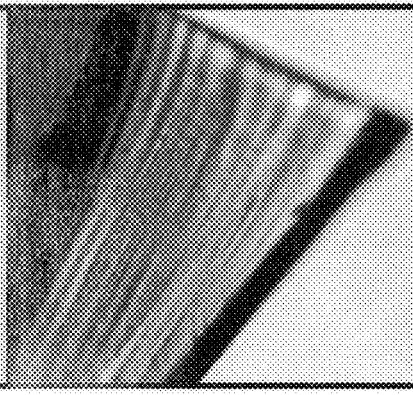
Figure 3:

Example 15: Interaction of Different Cellophil Copolymers with HEMA-Based Silicone Hydrogel Lenses During coating of HEMA-based silicone hydrogel lenses with various Cellophil copolymers significant differences in binding behavior were observed. It was surprisingly found that Cellophil copolymers comprising a principal monomer that was also present in the lens to be treated bound more strongly to that lens than Cellophil copolymers not containing such principal monomer. An example is illustrated in FIG. 3. In the experiment, 4 contact lenses that contained HEMA were incubated for 20 min at 116° C. either with Cellophil copolymers (1% (w/v) containing HEMA (HEMA (50 mol %)/AK(50 mol %), 72 kDa, PDI 3.1) or Cellophil containing n-isopropylacrylamide (NIPAAm) (NIPAAm(50 mol %)/AK(50 mol %), 75 kDa, PDI 2.9). Cellophil copolymer-treated lenses were further incubated in excess PBS (pH 7.4) for 3 or 6 h, respectively, or not so incubated. All lenses were then incubated in a ninhydrine solution which was heated to 95° C. for 2 h. Red-violet staining is indicative of the presence of amino acid-containing Cellophil copolymers. Results showed more durable staining of lenses treated with Cellophil copolymer containing HEMA than with Cellophil copolymer containing NIPAAm (FIG. 3 A). We concluded that Cellophil copolymer containing HEMA penetrated more efficiently and/or was retained better in a lens containing HEMA than Cellophil copolymer containing NIPAAm.

To analyze this effect in more detail, HEMA-based silicon hydrogel lenses coated with Cellophil copolymer as described above were stained with ninhydrine, cut manually and characterized by photo analysis. Cellophil copolymer containing HEMA but not the more hydrophobic Cellophil copolymer containing NIPAAm was able to penetrate into the contact lens during the coating procedure (FIGS. 3 C and D). It is suggested that the hydrogel parts of the lens may interact with the more hydrophilic Cellophil copolymer containing HEMA but not with the more hydrophobic Cellophil copolymer containing NIPAAm that may experience repulsion forces and therefore cannot penetrate deep into the lens. These surprising findings may be useful for the adaptation of Cellophil copolymers to specific lens materials leading to optimized performance in the coating process.

Example 16: Synthesis of a DMA/Acryloyl-L-Lysine/6-Acrylamido-2-Palmitamidohexanoic Acid Tri-Copolymer Using Free Radical Polymerization In a 20 ml reaction vessel N,N-Dimethylacrylamide (DMA) (0.26 ml, 2.52 mmol), acryloyl-L-lysine (63 mg, 0.315 mmol) and Nε-acryloyl-Nα-palmityl-L-Lysine (27.6 mg, 0.062 mmol) were dissolved in 15 ml deionized water, and TMEDA (0.07 ml, 0.464 mmol) was added. The solution was degased using an ultrasonic bath. Ammonium persulfate (APS) (6.62 mg, 0.029 mmol) was added to the degased solution. The polymerization reaction was performed for 4 h at room temperature and stopped by cooling the reaction vessel to 4° C. Thereafter, the copolymer was purified by extensive dialysis against deionized water using a dialysis tube with a 3.5 kDa MWCO. The purified copolymers were finally lyophilized and their average molecular weight (127 kDa) and PDI (2.7) were estimated by GPC). A detailed description of this method was presented in Example 14.

Example 17: Cellophil Block Copolymer Containing Lipid-Like Structures

Silicone and silicone hydrogel contact lens materials tend to bind proteins and lipids from the tear film during wear. Accumulation of protein and lipid deposits lead to a reduction of wear comfort and vision [19, 20]. In order to reduce these undesirable reactions, block copolymers were synthesized. The presence of these block copolymers on the lens surfaces was hypothesized to prevent lipid as well as protein deposition on the lens surfaces. The block copolymers contain first blocks comprising hydrophilic not-functionalized side chain-linked amino acids of formula I or formula II and second blocks comprising hydrophobic side chain-linked amino acids of formula I or formula II having their alpha-amino and/or carboxyl groups functionalized with alkyl or cholesteryl residues and other hydrophobic monomers. The alkyl or cholesterol residues should mimic the structures of lipids typically found in human tear fluids known to be responsible for the formation of harmful deposits on lens surfaces [21-23]. The block copolymers were expected to interact strongly with the silicone surfaces of contact lenses during the coating procedure. Saturation of the silicone lens surface with block copolymers should prevent lipid deposition. The hydrophilic blocks of the block copolymers will face away from the lens surfaces. Because they have a high capacity for binding water molecules, they should enhance surface wettability and lubricity of the lenses. The formed aqueous layer should function as an effective barrier against interaction with hydrophobic tear fluid lipids.

The above described hypothesis was first tested with a block copolymer that contained hydrophilic blocks comprising acryloyl-L-Lysine monomers and hydrophobic/lipophilic blocks comprising acrylated fatty-alcohol (iso-decylacrylate) and N,N-Dimethylacrylamide (DMA). Such block copolymers that contain hydrophilic blocks, i.e., blocks comprising one or more not-functionalized side chain-linked amino acid monomers of formula I and/or formula II, and hydrophobic blocks comprising one or more principal monomers are also encompassed by the present invention, as is the use of these copolymers in coating silicone hydrogel lenses.

Preparation of a Block Copolymer Containing a Hydrophilic Cellophil Polymer and a Lipid-Like Copolymer Using RAFT Polymerization Step A In a 50 ml round bottom flask, a solution of 2-(dodecyl-thiocarbonothioylthio)-2-methylpropionic acid (6.13 mg, 0.017 mmol), N,N-Dimethylacrylamide (0.624 ml, 6.05 mmol), and iso-decylacrylate (0.163 ml, 0.673 mmol) in 10 ml DMF was degased using ultrasonic treatment. Subsequently, 2-benzyl-2-(dimethylamino)-4'-morpholinobutyrophenone (6.40 mg, 0.017 mmol) was added, and polymerization was induced by UV light. After 4 h of polymerization under stirring, the reaction mixture was purified by extensive dialysis against deionized water using a membrane with a 3.5 kDa MWCO. The mixture was subsequently lyophilized. Average molecular weight (12 kDa) and PDI (1.19) of the block copolymer was verified by GPC measurement.

Step B

The lyophilized macro-CTA prepared in step A (300 mg, 6.82 µmol) was mixed with acryloyl-L-lysine (100 mg, 0.499 mmol) in 10 ml deionized water. The mixture was degassed using ultrasonic treatment. 2,2'-Azobis(2-methylpropionamidine) dihydro-chloride (4.62 mg, 0.017 mmol) was added to the mixture. Polymerization was induced by heating the mixture in a reaction vessel to 50° C. After 4 h of polymerization at 50° C., the resulting block copolymer was purified by extensive dialysis against deionized water using a membrane with a 3.5 kDa MWCO. The Cellophil block copolymer was subsequently lyophilized. Average molecular weight (18 kDa) and PDI (1.25) of the block-copolymer were verified by GPC measurement. The larger block copolymers (32 kDa, PDI 1.28; 58 kDa, PDI 1.24) were obtained by decreasing the ratio of CTA to monomers in step A from 1/100 to 1/200 (32 kDA) and 1/400 (58 kDa), respectively, whereas the molar ratios of iso-decylacrylate (7.5 mol %), DMA (63.9 mol %) and AK (28.6 mol %) were kept constant.

The effect of these Cellophil block copolymers on the wettability of silicone hydrogel contact lenses was tested by measurement of contact angles. A low contact angle indicates a good surface wettability. For this experiment Narafilcon A-based lenses were coated with 18 kDa, 32 kDa or 58 kDa Cellophil block copolymer. To achieve this coating, lenses were incubated for 20 min at 116° C. in a 1% (w/v) solution of Cellophil block copolymer and were then slowly cooled to room temperature. After this coating the lenses were incubated for 10 min at room temperature in 5 ml PBS under slight agitation to remove excess block copolymer and were air-dried for 24 h. Subsequently, small rectangular pieces (0.5×0.5 cm) were cut out from the lenses using a sharp knife. The latter lens pieces were mounted on an adhesive film that had been placed on a fat-free glass slide, which slide was introduced into a drop profile analyzer (CAM-100, KSV Instruments, Helsinki, Finland). For measurements, a small drop of water was placed on the materials using a narrow-gauged needle. Contact angles of drops were estimated by photo analysis using CAM2008 software (KSV Instruments). Pieces similarly obtained from not-coated lenses served as controls.

Figure 4:
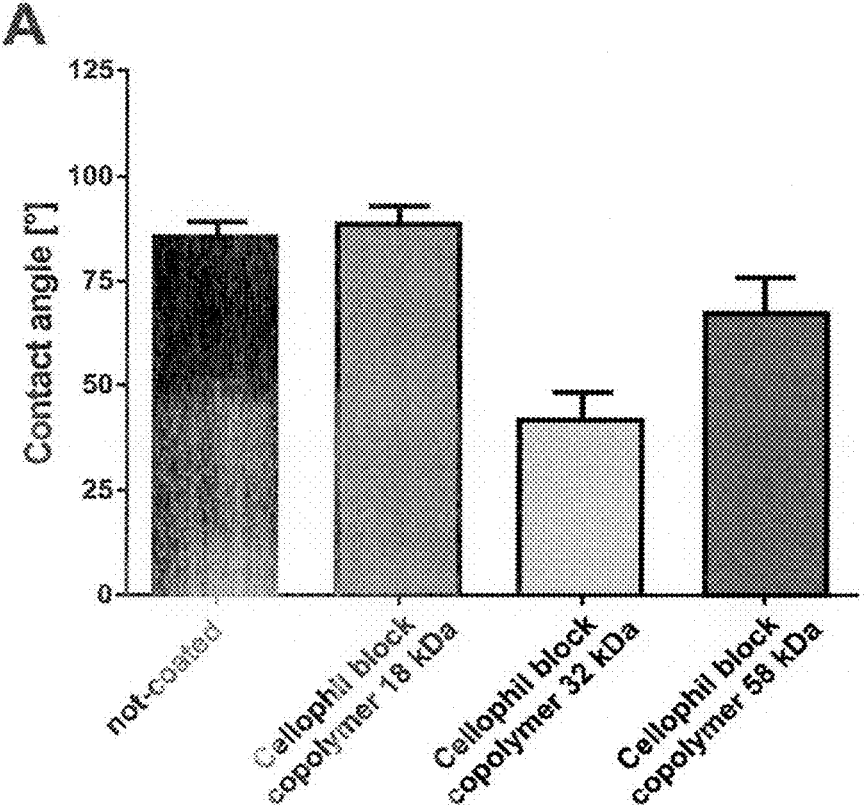
FIG. 4. Contact angle measurements of silicone hydrogel contact lenses (Narafilcon A) coated with Cellophil block copolymers. A: Contact angles of contact lenses left uncoated or coated with Cellophil block copolymers of differing molecular sizes. Data represent the mean and SD of 4 contact lenses. B: Visual representation of results.
Figure 4:
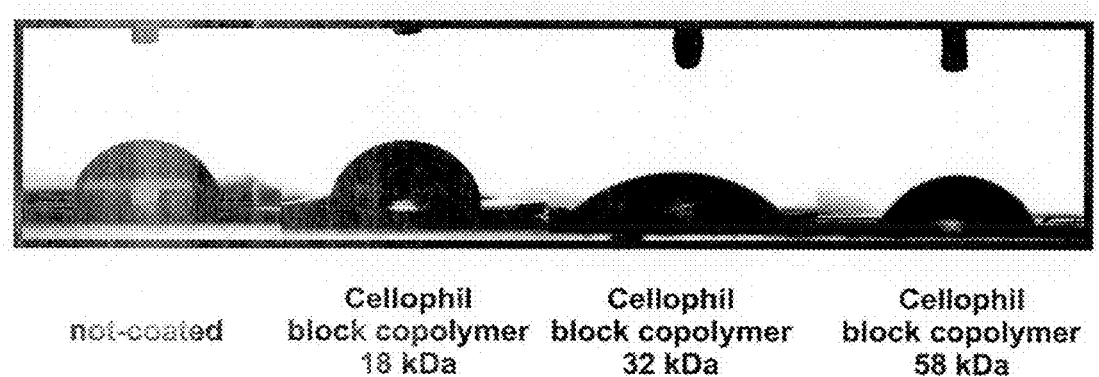

The results of this experiment are presented in FIG. 4 A. Data represent mean contact angles and standard deviations for four lenses. In part B of the figure the decrease of the contact angle with different coatings is illustrated by means of representative images. The data show that coating with Cellophil block copolymers containing lipid-like blocks can decrease contact angles, indicating an increased wettability of the lens surfaces. The effect was dependent on block copolymer size. Whereas small block copolymers of approx. 18 kDa showed no significant effect on wettability, significant improvements were seen with block copolymers of higher molecular weight (32 kDa and 58 kDa). Between these, the 32 kDa copolymer showed the greater reduction of the contact angle. This suggests that optimal block-copolymer size for best effects on wettability is above 18 Kda.

Other block copolymers were prepared containing first blocks comprising hydrophilic blocks comprising acryloyl-L-Lysine monomers and hydrophobic/lipophilic blocks comprising NE-acryloyl-Na-palmityl-L-Lysine (AK-PAL) and N,N-Dimethylacrylamide (DMA) containing different amounts of hydrophobic monomer of formula I were synthesized. This results in the block copolymers:

MH02 [DMA (90.6% mol)/AK-PAL(0.6% mol)/AK (9.9% mol], PDI 1.26;
MH03 [DMA (90.1% mol)/AK-PAL(1.1% mol)/AK (8.8% mol], PDI 1.26;
MH04; [DMA (89.6% mol)/AK-PAL(1.6% mol)/AK (8.8% mol], PDI 1.28;

MH05; [DMA (84.0% mol), AK-PAL(0.5% mol)/AK (15.5% mol], PDI 1.29,

MH06 [DMA (83.6% mol), AK-PAL(1.1% mol)/AK (15.4% mol], PDI 1.25.

MH07 [DMA (83.2% mol), AK-PAL(1.5% mol)/AK (15.3% mol], PDI 1.25.

The sizes of the above block-copolymers were determined by Matrix-assisted laser desorption/ionization (MALDI) to be about 8 kDa (8-10 kDa). For technical information on MALDI, the reader is referred to Karas, M. and Kruger, R. (2003) Ion formation in MALDI: the cluster ionization mechanism. Chem. Rev. 103(2): 427-40.

The binding behavior of these block copolymers was tested by coating three different commercially available silicone hydrogel lens materials (Air optics Aqua®/Lotrafilcon B; Pure Vision®/Balafilcon A and Biofinity®/Comfilcon A). For this assay lenses were incubated for 20 min at 116° C. in a 1% (w/v) solution of Cellophil block copolymers and then slowly cooled to room temperature. After this coating the lenses were incubated for 10 min at room temperature in 5 ml PBS under slight agitation to remove excess block copolymers. Not-coated lenses were used controls. The coated and control lenses were subsequently incubated for 2 hours at 37° C. in a 0.01% (w/v) solution of picrylsulfonic acid in water that reacts with primary amino groups in Cellophil copolymers to form yellow conjugates. The amounts of Cellophil copolymers bound to the lens surface were subsequently estimated by visual inspection. The experiment confirmed that Cellophil copolymer has to be adapted/optimized with respect to the lens material that is to be coated: Cellophil copolymers bound differently to the three lens materials. As example, Cellophil copolymer MH05 showed strong binding to the Comfilcon A and Balafilcon A lens materials but poor binding to the Lotrafilcon B lens material. Notwithstanding these differences, lower ratios of hydrophilic monomer of formula I to hydrophobic monomer of formula I in the block copolymers generally correlated with better binding to the lens surface.

Two longer versions of block-copolymer MH04 were synthesized by decreasing the ratio of CTA to monomers in the first polymerization reaction as described before. The sizes of these block-copolymers were estimated to be about 16 kDa and 24 kDa, respectively. Silicon hydrogel lenses were coated with each of the three differently sized MH04 block-copolymers, stained with picrylsulfonic acid and analyzed as discussed in the preceding section. Whereas the 8 kDa MH04 block-copolymer penetrated well into the lens, much less staining/penetration was observed with the 16 kDa and 24 kDa block-copolymers. The experiments detailed below utilized exclusively 8-kDa block-copolymers.

Figure 5:
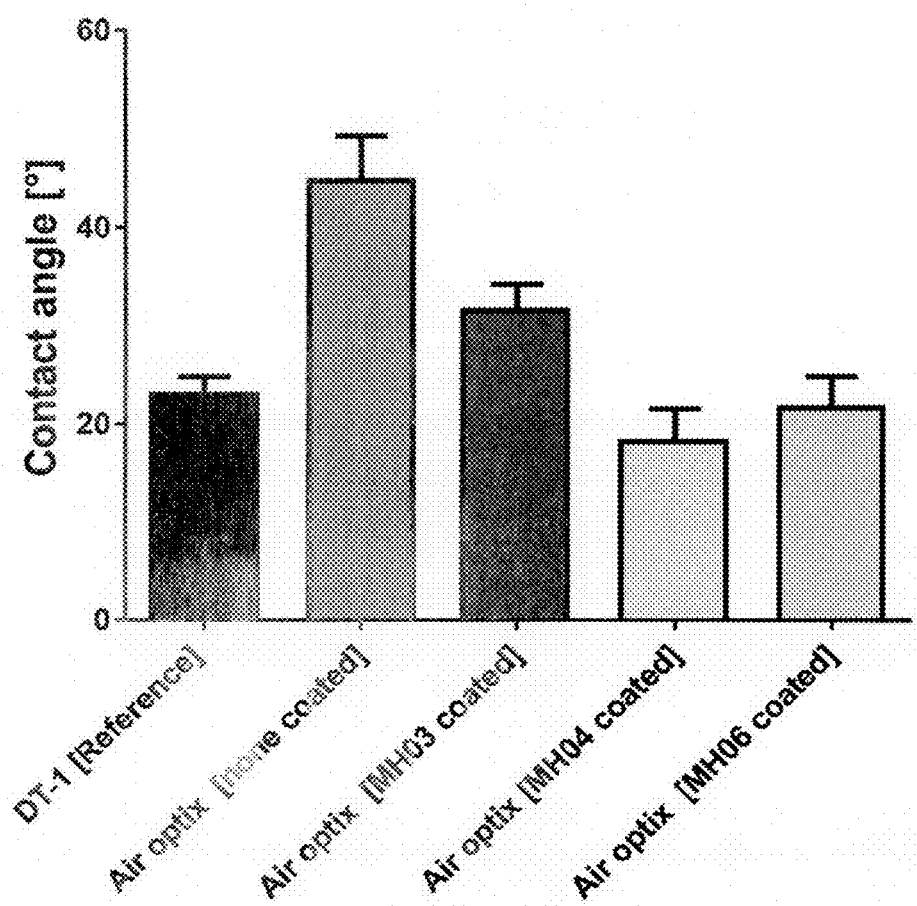
FIG. 5. Contact angle measurements on Lotrafilcon B silicone hydrogel lenses (Air Optix Aqua®, Alcon) left uncoated or coated with Cellophil block copolymers MH03, MH04 or MH06. Daily total 1® lenses (DT-1, Alcon) directly out of their package solution served as references. Data represent the mean and SD of 5 contact lenses.

The wettability effects of Cellophil block-copolymers MH03, MH04 and MH06 (which copolymers had shown good binding to Lotrafilcon A (Air optics Aqua®, Alcon) silicone hydrogel lenses) were determined by contact angle measurements using a similar protocol as that described above. The wettability of Lotrafilcon A lenses that had been coated with a Cellophil block copolymer or that had been left uncoated was compared to daily total One® (DT-1) lenses out of the package solution and air dried for 24 h prior to measurement. DT-1 is known to have the best surface wettability of all commercially available silicone hydrogel contact lenses. To simulate the environment in the eye, these measurements were performed in synthetic tear fluid (according to [24] but without lipid mixture). Results are presented in FIG. 5. All tested Cellophil copolymers significantly improved surface wettability compared to the uncoated control. Coating of Lotrafilcon A lenses with Cellophil block copolymers MH04 and MH 06 resulted in contact angles that were comparable to that seen with DT-1. Cellophil copolymer MH04 was chosen for further tests.

To further elucidate the performance of the coating process, microtribological measurements were performed that analyzed coefficients of frictions of coated contact lenses. Lotrafilcon A silicone hydrogel lenses (Air optix Aqua®, Alcon) were incubated in PBS (pH 7.4, 10 ml per lens) for 6 h at room temperature to remove potential surfactants from the original packaging solution. The lenses were subsequently placed in a solution of the Cellophil lipid block-copolymer MH 04 (1% w/v of PBS) or in PBS (pH 7.4, =Blank) in a 1.5 ml reaction tube (one lens per tube) and incubated at 116° C. for 20 min.

Afterwards the solution was slowly cooled down to room temperature. Coated and not-coated lenses were analyzed on a microtribometer (BASALT®-MUST Precision Tester, TETRA GmbH, Ilmenau, Germany). A lens to be analyzed was placed into a lens container. The backside of the lens was gently blotted with precision wipes and the lens placed into a spherical sample holder (r=8.6 mm). After a period of 60 seconds to allow the lens to form a tight contact with the surface of the holder, the holder was mounted in the tribometer. 100 µl of a synthetic tear fluid (see above) were placed in the contact area between the spherical holder and the fixed counter body forming a capillary bridge. As counter body a PET film served (Good Fellow, 0.1 mm thickness, 20 mm width, transparent, biaxially oriented). The PET film was previously fixed with cyanoacrylate glue onto a microscopic glass slide. The glue was applied at the beginning and the end of the stripe to avoid uneven contact area. Measurements were performed by moving the holder with a load of 30 mN and a speed of 30 mm/min over a distance of 10 mm on the fixed counter body. For a complete measurement 10 forth and back cycles were performed. The last 7 cycles were used for data analysis. These datasets included the values of the turning points so that the obtained friction coefficients represented an average of dynamic and static friction. Lotrafilcon A (Air optics Aqua®, Alcon) and Daily total One® (DT-1) silicone hydrogel lenses out of the package solution served as references. 10 lenses for each condition were analyzed. The results of this experiment are represented graphically in FIG. 6. Cellophil copolymer-coating significantly (p value=$2.97 \times 10^{-5}$) reduced the coefficient of friction if compared with the not-coated contact lenses (Blank). Specifically, the coating reduced the mean value of friction from 0.133+/−0.039 to 0.035+/−0.016, approaching the values for DT-1 contact lenses directly out of the package (0.019+/−0.004). A double side t-test revealed no significant statistical differences between those two groups (Cellophil coated Lens vs. DT-1; p value=0.06). Not-coated Air Optix lenses (Blank) and Air Optix lenses directly out of the package showed no significant difference in friction coefficient (p value=0.55). This indicates that the procedure (washing and autoclaving with PBS) did not significant reduce the performance of the not-coated contact lenses. Therefore, the reduced friction (=increased lubricity) was truly a direct result of the Cellophil copolymer-coating.

Example 18: Synthesis of 6- and 4-Arm RAFT Agents

The following protocol describes a general procedure for the synthesis of multiarm RAFT agents that are useful for the generation of multiarm Cellophil copolymers. A person who is skilled in art will be able change the parameters in order to obtain variants of these multiarm RAFT agents useful for a specific application, e.g., exchanging the RAFT precursor molecule or core structure.

A solution of 2-bromopropionyl bromide (10.97 mL, 105.00 mmol) in tetrahydrofuran (30 mL) was added to a suspension of dipentaerythritol (4.00 g, 15.73 mmol) in triethylamine (14.61 mL, 105.00 mmol) and tetrahydrofuran (100 mL) at 0° C. under nitrogen. The resulting suspension was allowed to warm to room temperature and was stirred for 16 h. Solids were removed by filtration, and the solvent of the filtrate was evaporated under reduced pressure. The residue was dissolved in ethyl acetate (150 mL), washed successively with water (2×50 mL), saturated aqueous sodium bicarbonate (2×50 mL), water (2×50 mL) and brine (50 mL). The organic phase was separated, dried over sodium sulfate and concentrated in vacuo, resulting in an orange oil. Crystallization from diethyl ether afforded dipentaerythritol hexakis(2-bromopropionate) (2.00 g, 12%) as a white solid.

A solution of carbon disulfide (0.95 mL, 15.79 mmol) in diethyl ether (13 mL) was added to a suspension of sodium ethanethiolate (1.11 g, 13.16 mmol) in diethyl ether (40 mL) at room temperature, and the reaction mixture was stirred for 2 h at room temperature. The solvent was removed in vacuo. The residue was dissolved in ethyl acetate (8 mL) and a suspension of dipentaerythritol hexakis(2-bromopropionate) (1.00 g, 0.94 mmol) in ethyl acetate (1.5 mL) was added dropwise at room temperature. The suspension was further stirred for 4 h at room temperature and quenched with brine (10 mL). The aqueous phase was separated and extracted with ethyl acetate (3×15 mL). The combined organic phases were washed with water (2×20 mL), aqueous hydrochloric acid (2×15 mL), water (15 mL) and brine (20 mL). The organic phase was separated, dried over sodium sulfate and concentrated under reduced pressure. Purification by column chromatography (SiO$_2$, n-hexane/ethyl acetate, 4:1, v/v) afforded the 6-arm RAFT initiator (1.00 g, 76%) as a yellow oil.

The same procedure as described for the synthesis of dipentaerythritol hexakis(2-bromopropionate) was applied for the synthesis of pentaerythritol tetrakis (2-bromoprionate). Pentaerythritol (3.00 g, 22.04 mmol) was allowed to react with 2-bromopropionyl bromide (9.92 mL, 95.00 mmol) in the presence of triethylamine (13.22 mL, 95.00 mmol). Crystallization from diethyl ether afforded pentaerythritol tetrakis (2-bromoprionate) (5.10 g, 34%) as a white solid.

A solution of ethanethiol (1.92 mL, 26.60 mmol) in water (4 mL) was stirred for 10 minutes at 0° C. Afterwards a solution of sodium hydroxide (1.08 g, 26.9 mmol) in water (1.08 mL) was added dropwise, followed by addition of acetone (1.5 mL). The solution was stirred for 30 min at room temperature and cooled down to 0° C. again. A solution of pentaerythritol tetrakis(2-bromopropionate) (3.00 g, 4.44 mmol) in dichloromethane (10 mL) was added, and the reaction mixture was stirred for 48 h at room temperature. The suspension was filtered and the filtrate was diluted with ethyl acetate (50 mL). The organic phase was separated and washed with water (2×20 mL), aqueous hydrochloric acid (2×15 mL), water (15 mL) and brine (20 mL). After drying with sodium sulfate the organic phase was filtered and concentrated in vacuo. Purification by column chromatography (SiO2, n-hexane/ethyl acetate, 4:1, v/v) afforded the 4-arm RAFT initiator (3.20 g, 80%) as yellow oil.

All products were verified by NMR measurements. Synthesis protocols were adapted from refs. [25-27].

Example 19: Synthesis of a 32 Arm Dentrimer RAFT Agent

The following protocol describes a general procedure for the synthesis of a dentrimeric RAFT agent that is useful for the generation of dentrimer derivatives of Cellophil copolymers.

In a 50-ml reaction vessel 1-chloro-2-methyl-1-oxopropan-2-yl ethyl carbonotrithioate (0.75 g, 3.09 mmol) was dissolved in 2 ml chloroform. To this solution PEG136-DEOH32 (0.458 g, 0.048 mmol; Sigma Aldrich, Buchs, Switzerland) in 25 ml chloroform was added and the mixture incubated for 30 minutes at room temperature. Subsequently, triethylamine (0.215 ml, 1.544 mmol) was added and the mixture incubated for an additional 30 minutes. Afterwards, the solvent was removed under reduced pressure and the residue washed with water (50 ml). The resulting emulsion was centrifuged and the upper phase removed. To the residual material tert-Butylmethylether (tBME) (50 ml) was given, mixed by shaking and the resulting emulsion separated by centrifugation. Finally, the product was dried over sodium hydroxide under reduced pressure at 40° C. (0.2 g, 0.012 mmol; yield 25.8%). The product was verified by NMR measurements.

Example 20: Synthesis of a 6 Arm Cellophil DMA/AK-PAL/AK Tri-Block-Copolymer

A solution of the 6-arm RAFT agent (example 18) (20 mg, 1.4 µmol) in 10 ml DMF and DMA (1.756 ml, 17.04 mmol) was degassed in a ultrasound bath, and polymerization was started by addition of AIBN (4.66 mg, 0.028 mmol) and heating to 60° C. After 6 h, the resulting 6-arm polymer was precipitated with tBME and dried at 40° C. under reduced pressure.

The purified macro-RAFT agent (1 g, 8.33 µmol) was subsequently used in a second polymerization with NE-acryloyl-Na-palmityl-L-Lysine (73 mg, 167 µmol) and 2,2'Azobis(2-methylpropionamidine)dihydrochloride (2.26 mg, 8.33 µmol) in 10 ml water. Polymerization was induced by heating to 45° C. and continued for 6 h. The resulting 6-arm DMA/AK-PAL block copolymer was purified by dialysis using a 3.5 MWCO membrane and lyophilized. This 6-arm DMA/AK-PAL block copolymer was then be used as a macro-RAFT agent for the addition of a third hydrophilic acryloyl-L-lysine block using the same polymerization and purification procedures but substituting NE-acryloyl-Na-palmityl-L-Lysine with acryloyl-L-lysine.

Example 21: Synthesis of methyl 6-acrylamido-2-dodecanamidohexanoate

In a two-necked flask with intensive condenser AK-Lau (synthesized according to a procedure presented in example 10) (1 g, 2.61 mmol) was dissolved in 15 ml DMF. To this solution sodium carbonate (0.554 g, 5.24 mmol) was given. Subsequently, iodine methane (0.654 ml, 10.46 mmol) was added dropwise through a septum. The reaction was stirred overnight at room temperature before 20 ml of ethyl acetate were added. The organic phase was washed two times with deionized water and brine, dried over $Na_2SO_4$ and solvents were removed by vacuum till dryness. The solid product was then dissolve in ethyl acetate and filtered through activated carbon to remove residual iodine. The solvent was removed in vacuum to obtain pure methyl 6-acrylamido-2-dodecanamidohexanoate (0.7 g, yield 67.5%). The product was verified by NMR measurements.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e. g., all exact exemplary values provided with respect to a particular factor or measurement can be considered to also provide a corresponding approximate measurement, modified by "about," where appropriate).

The use of any and all examples, or exemplary language (e.g., "such as") provided herein is intended merely to better illuminate the invention and does not pose a limitation on the scope of the invention unless otherwise indicated.

The citation and incorporation of patent documents herein is done for convenience only and does not reflect any view of the validity, patentability and/or enforceability of such patent documents. The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context (e. g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent documents cited in this specification are herein incorporated by reference in their entireties as if each individual publication or patent document were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The invention claimed is:

1. A copolymer made from a polymerization mixture comprising
   (a) one or more polymerizable principal monomers, which monomers are characterized as having at least one vinylic group and not containing an amino acid residue,
   (b) one or more not-functionalized co-principal monomers of formula I and/or formula II wherein Y and Z are both H and A is —O—,

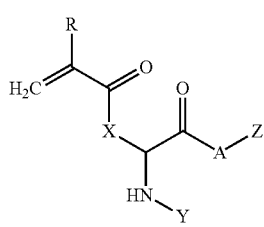

Formula I

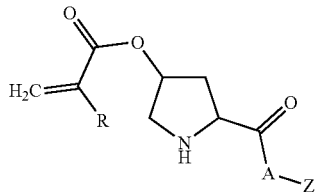

Formula II wherein: R is —H, —$CH_3$, —$CH_2$—$CH_3$, —$(CH_2)_2$—$CH_3$; X is —NH$(CH_2)_4$—, —NH$(CH_2)_3$—, —O—$C_6H_4$—$CH_2$—, —O—$CH_2$—, —O—CH($CH_3$)—, —S—$CH_2$—, —NH—$C_6H_4$—$CH_2$—; Y is H, —CO—$C_nH_{2n+1}$, —CO—$C_mH_{2m-1}$, —CO—$C_pH_{2p-3}$, —CO—$C_qH_{2q-5}$ (with n=1-22, m=3-22, p=9-22, q=15-22) or —CO-cholesten; Z is H, —$C_nH_{2n+1}$, —$C_mH_{2m-1}$, —$C_pH_{2p-3}$, —$C_qH_{2q-5}$ (with n=1-22, m=3-22, p=9-22, q=15-22); and A is —O— or —NH—, (c) one or more functionalized co-principal monomers of formula I and/or formula II wherein Y and/or Z are not H,
   (d) a free radical initiator and, optionally,
   (e) a chain-transfer-agent.

2. The copolymer of claim 1 wherein the copolymer is a block copolymer comprising hydrophobic and hydrophilic blocks containing amino acid groups, the block copolymer made by
   (a) polymerization of a reaction mixture comprising one or more polymerizable principal monomers not containing an amino acid group, one or more co-principal monomers of formula I and/or formula II with the proviso that at least one of Y and Z is not H, a free radical initiator and optionally a chain-transfer-agent (CTA), the polymerization yielding hydrophobic copolymers and
   (b) polymerization of a reaction mixture comprising one or more co-principal monomers of formula I and/or formula II with the proviso that Y and Z are H and A is —O—, a free radical initiator and, optionally, one or more polymerizable principal monomers not containing an amino acid group and/or a chain-transfer-agent (CTA), the polymerization yielding hydrophilic polymers or copolymers;
   whereby the two polymerizations are carried out sequentially, the reaction mixture of the later of the polymerizations further comprising the polymer or copolymer resulting from the earlier polymerization.

3. The copolymer of claim 1 wherein the total amount of monomers of formula I and/or formula II ranges from 1% to 49.9% (mol) of all monomers contained in the copolymer.

4. The copolymer of claim 1, wherein the total amount of monomers of formula I and/or formula II ranges from 5% to 35% (mol) of all monomers contained in the copolymer.

5. The copolymer of claim 1, wherein the copolymer is a multiarm copolymer or block copolymer with 3 to 8 linear polymer, copolymer or block copolymer chains.

6. The copolymer of claim 1, wherein the copolymer has a dendronized structure with 8 to 32 attached linear polymer, copolymer or block copolymer chains.

7. A silicone hydrogel contact lens coated with or comprising a leachable copolymer of claim 1.

8. The silicone hydrogel contact lens of claim 7, wherein the leachable copolymer elutes from the lens surfaces during lens wear and lubricates these surfaces for a period of up to 60 days.

9. The silicone hydrogel contact lens of claim 8, wherein the leachable copolymer elutes from the lens surfaces during lens wear and lubricates these surfaces for a period of 12-24 hours.

10. The silicone hydrogel contact lens of claim 8, wherein the leachable copolymer elutes from the lens surfaces during lens wear and lubricates these surfaces for a period of at least seven days.

11. The silicone hydrogel contact lens of claim 7, wherein the leachable copolymer has an average molecular weight of 5,000 Daltons to 120,000 Daltons.

12. The silicone hydrogel contact lens of claim 7, wherein at least 80% (w) of the leachable copolymer molecules have an average molecular weight of 5,000 Daltons to 120,000 Daltons.

13. The silicone hydrogel contact lens of claim 7, wherein the leachable copolymer is present in an amount from 0.1% to 20% (w) of all polymeric material contained in the hydrated lens.

14. A method for preparing a silicone hydrogel contact lens coated with a leachable copolymer of claim 1, comprising the steps of
(a) preparing the copolymer and
(b) exposing a silicone hydrogel contact lens to an aqueous composition comprising the copolymer of step (a) under conditions under which the copolymer penetrates into the lens.

15. A method for preparing a silicone hydrogel contact lens comprising a copolymer of claim 1, comprising the steps of
(a) preparing the copolymer and
(b) polymerizing silicone hydrogel lens-forming material in the presence of the copolymer of step (a).

16. The method of claim 14, wherein a silicone hydrogel contact lens is exposed to an aqueous solution comprising the copolymer for 10-30 min at a temperature of 110-134° C.

17. The method of claim 16, wherein the aqueous solution comprises the copolymer at a concentration of 0.25-10% (w/v).

18. The method of claim 15, wherein the copolymer is present during polymerization in an amount not exceeding 20% (w) of all monomers, macromers and polymers.

* * * * *